US008759275B2

(12) United States Patent
Smets et al.

(10) Patent No.: US 8,759,275 B2
(45) Date of Patent: Jun. 24, 2014

(54) HIGH-EFFICIENCY PERFUME CAPSULES

(75) Inventors: Johan Smets, Lubbeek (BE); Pascale Claire Annick Vansteenwinckel, Weerde (BE); Yonas Gizaw, West Chester, OH (US); Frank Hulskotter, Bad Duerkheim (DE); Dieter Boeckh, Limburgerhof (DE); Hans-Joachim Haehnle, Neustadt (DE)

(73) Assignee: The Proctor & Gamble Company, Cincinnati, OH (US)

( * ) Notice: Subject to any disclaimer, the term of this patent is extended or adjusted under 35 U.S.C. 154(b) by 0 days.

(21) Appl. No.: 12/939,757

(22) Filed: Nov. 4, 2010

(65) Prior Publication Data

US 2011/0111999 A1 May 12, 2011

Related U.S. Application Data

(60) Provisional application No. 61/258,874, filed on Nov. 6, 2009, provisional application No. 61/258,900, filed on Nov. 6, 2009, provisional application No. 61/311,928, filed on Mar. 9, 2010.

(51) Int. Cl.
| | | |
|---|---|---|
| *C11D 17/00* | (2006.01) | |
| *C11D 17/06* | (2006.01) | |
| *C11D 3/50* | (2006.01) | |
| *C11D 3/60* | (2006.01) | |
| *C11D 11/00* | (2006.01) | |
| *A61K 8/11* | (2006.01) | |
| *D06L 1/16* | (2006.01) | |
| *B08B 7/00* | (2006.01) | |
| *A61K 8/81* | (2006.01) | |
| *A01N 25/28* | (2006.01) | |
| *A61K 8/73* | (2006.01) | |
| *C09B 67/02* | (2006.01) | |
| *B01J 13/22* | (2006.01) | |
| *A23L 1/22* | (2006.01) | |
| *A23L 1/00* | (2006.01) | |
| *A61Q 19/00* | (2006.01) | |

(52) U.S. Cl.
CPC .......... *C11D 17/0039* (2013.01); *A61K 8/8147* (2013.01); *A01N 25/28* (2013.01); *A61K 8/731* (2013.01); *C11D 3/505* (2013.01); *A61K 2800/412* (2013.01); *C09B 67/0097* (2013.01); *B01J 13/22* (2013.01); *A61K 8/11* (2013.01); *A23L 1/22016* (2013.01); *A23L 1/0029* (2013.01); *A61Q 19/00* (2013.01)
USPC ........... 510/441; 510/101; 510/108; 510/119; 510/221; 510/337; 510/349; 510/418; 510/444; 510/445; 510/513; 510/515; 510/516; 424/408; 424/417; 512/4; 134/42; 8/137

(58) Field of Classification Search
USPC ......... 510/441, 445, 101, 349, 475, 513, 516, 510/108, 119, 221, 337, 418, 444, 515; 424/408, 417; 512/4; 134/42; 8/137
See application file for complete search history.

(56) References Cited

U.S. PATENT DOCUMENTS

| | | | |
|---|---|---|---|
| 4,430,243 A | 2/1984 | Bragg | |
| 4,515,705 A | 5/1985 | Moeddel | |
| 4,537,706 A | 8/1985 | Severson, Jr. | |
| 4,537,707 A | 8/1985 | Severson, Jr. | |
| 4,550,862 A | 11/1985 | Barker et al. | |
| 4,561,998 A | 12/1985 | Wertz et al. | |
| 4,597,898 A | 7/1986 | Vander Meer | |
| 4,968,451 A | 11/1990 | Scheibel et al. | |
| 5,486,303 A | 1/1996 | Capeci et al. | |
| 5,489,392 A | 2/1996 | Capeci et al. | |
| 5,516,448 A | 5/1996 | Capeci et al. | |
| 5,565,145 A | 10/1996 | Watson et al. | |
| 5,565,422 A | 10/1996 | Del Greco et al. | |
| 5,569,645 A | 10/1996 | Dinniwell et al. | |
| 5,574,005 A | 11/1996 | Welch et al. | |
| 5,576,282 A | 11/1996 | Miracle et al. | |
| 5,595,967 A | 1/1997 | Miracle et al. | |
| 5,597,936 A | 1/1997 | Perkins et al. | |
| 5,691,297 A | 11/1997 | Nassano et al. | |
| 5,879,584 A | 3/1999 | Bianchetti et al. | |
| 5,929,022 A | 7/1999 | Velazquez | |
| 6,132,558 A | 10/2000 | Dyllick-Brenzinger et al. | |
| 6,225,464 B1 | 5/2001 | Hiler, II et al. | |
| 6,277,404 B1 | 8/2001 | Laversanne et al. | |
| 6,294,514 B1 | 9/2001 | Welling | |
| 6,306,812 B1 | 10/2001 | Perkins et al. | |
| 6,326,348 B1 | 12/2001 | Vinson et al. | |

(Continued)

FOREIGN PATENT DOCUMENTS

| | | | |
|---|---|---|---|
| EP | 1 533 364 A2 | 5/2005 | |
| EP | 1797947 A2 * | 6/2007 | |

(Continued)

OTHER PUBLICATIONS

International Search Report; International Application No. PCT/US2010/055393; date of mailing Feb. 23, 2011; 5 pages.

*Primary Examiner* — Lorna M Douyon
(74) *Attorney, Agent, or Firm* — James F. McBride; Steven W. Miller

(57) ABSTRACT

The present application relates to high efficiency particles and compositions, such as consumer products, comprising such high efficiency particles as well as processes for making and using such high efficiency particles and compositions comprising such high efficiency particles. Such high efficiency particles and compositions provide enhanced benefit agent delivery to a situs that is treated with such high efficiency particles and compositions.

17 Claims, No Drawings

(56) References Cited

U.S. PATENT DOCUMENTS

| | | | |
|---|---|---|---|
| 6,376,445 B1 | 4/2002 | Bettiol et al. | |
| 6,544,926 B1 | 4/2003 | Bodmer et al. | |
| 6,592,990 B2 | 7/2003 | Schwantes | |
| 6,869,923 B1 | 3/2005 | Cunningham et al. | |
| 7,119,057 B2 * | 10/2006 | Popplewell et al. | 510/438 |
| 1,797,947 A1 | 6/2007 | Anastasiou et al. | |
| 7,723,453 B2 | 5/2010 | Carnali et al. | |
| 2003/0109401 A1 | 6/2003 | Housmekerides et al. | |
| 2004/0214742 A1 | 10/2004 | Meli et al. | |
| 2006/0172909 A1* | 8/2006 | Schmiedel et al. | 510/267 |
| 2006/0287205 A1 | 12/2006 | Popplewell et al. | |
| 2007/0004610 A1* | 1/2007 | Brain et al. | 510/130 |
| 2007/0123442 A1 | 5/2007 | Holzner et al. | |
| 2007/0202063 A1 | 8/2007 | Dihora et al. | |
| 2007/0233026 A1 | 10/2007 | Roe et al. | |
| 2008/0118568 A1* | 5/2008 | Smets et al. | 424/489 |
| 2008/0164678 A1* | 7/2008 | White | 280/504 |
| 2009/0209661 A1 | 8/2009 | Somerville Roberts et al. | |
| 2009/0226529 A1 | 9/2009 | Quellet et al. | |
| 2009/0247449 A1 | 10/2009 | Burdis et al. | |
| 2009/0256107 A1* | 10/2009 | Hentze et al. | 252/73 |
| 2009/0289216 A1* | 11/2009 | Jung et al. | 252/79 |
| 2010/0305021 A1 | 12/2010 | Dykstra | |
| 2011/0086788 A1 | 4/2011 | Smets et al. | |
| 2011/0107524 A1 | 5/2011 | Chieffi et al. | |
| 2011/0110993 A1 | 5/2011 | Chieffi et al. | |
| 2011/0110997 A1 | 5/2011 | Cunningham et al. | |
| 2012/0177924 A1* | 7/2012 | Jung et al. | 428/402.24 |

FOREIGN PATENT DOCUMENTS

| | | |
|---|---|---|
| JP | 1 168337 A | 7/1989 |
| WO | WO 00/32601 A2 | 6/2000 |
| WO | WO 01/41915 A1 | 6/2001 |
| WO | WO 01/87475 A1 | 11/2001 |
| WO | WO 2008/006762 A2 * | 1/2008 |
| WO | WO 2008/046839 A1 * | 4/2008 |

* cited by examiner

HIGH-EFFICIENCY PERFUME CAPSULES

CROSS-REFERENCES TO RELATED APPLICATIONS

This application claims priority under 35 U.S.C. §119(e) to U.S. Provisional Application Ser. No. 61/258,874, filed Nov. 6, 2009, U.S. Provisional Application Ser. No. 61/258,900, filed Nov. 6, 2009, and U.S. Provisional Application Ser. No. 61/311,928, filed Mar. 9, 2010.

FIELD OF INVENTION

The present application relates to high efficiency encapsulates and compositions, such as consumer products, comprising such high efficiency encapsulates as well as processes for making and using such high efficiency encapsulates and compositions comprising such high efficiency encapsulates.

BACKGROUND OF THE INVENTION

Benefit agents, such as perfumes, silicones, waxes, flavors, vitamins and fabric softening agents, are expensive and/or generally less effective when employed at high levels in consumer products, for example, personal care compositions, cleaning compositions, and fabric care compositions. As a result, there is a desire to maximize the effectiveness of such benefit agents. One method of achieving such objective is to improve the delivery efficiencies of such benefit agents. Unfortunately, it is difficult to improve the delivery efficiencies of benefit agents as such agents may be lost do to the agents' physical or chemical characteristics, or such agents may be incompatible with other compositional components or the situs that is treated.

One method of improving the delivery efficiency of a benefit agent is to encapsulate such benefit agent. While such efforts may improve the delivery efficiency of the benefit agent, further delivery efficiency improvements are desired as encapsulated benefit agents may be lost before or after they are applied to the situs of interest due to factors such as mechanical or chemical interactions, for example the action of wash and or rinse liquors, and/or charge interactions. In certain applications, the deposition of encapsulated benefit agents is improved by coating the encapsulated benefit agent with a polymers. In general, such polymer coating improves the deposition of the encapsulates. However, when multiple surfaces are treated simultaneously, for example, a load of laundry containing a variety of fabrics, each surface is typically treated to a different degree (more or less benefit agent being delivered). For cases where the benefit agent is a perfume, the different treatment levels on the different fabrics of a wash load, can lead to too strong odor on some fabrics and to too weak an odor on other fabrics. Applicants recognized that the source of the unequal treatment problem was primarily due to preferential encapsulate deposition that was driven by the polymeric deposition aid. Thus what is needed are encapsulated benefit agents that have a high and even deposition profile across multiple different surfaces.

In the present application, Applicants disclose encapsulated benefit agents and specific classes of amine containing polymers that, when combined, provide a high and even deposition profile across multiple different surfaces, for example, hair, skin, and multiple fabrics such as cotton, high surface cottons, polycotton and polyester.

SUMMARY OF THE INVENTION

The present application relates to high efficiency encapsulates and compositions, such as consumer products, comprising such high efficiency encapsulates as well as processes for making and using such high efficiency encapsulates and compositions comprising such high efficiency encapsulates.

DETAILED DESCRIPTION OF THE INVENTION

Definitions

As used herein "consumer product" means baby care, beauty care, fabric & home care, family care, feminine care, health care, snack and/or beverage products or devices generally intended to be used or consumed in the form in which it is sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshing), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning and/or treatment composition" is a subset of consumer products that includes, unless otherwise indicated, beauty care, fabric & home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshing), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshing that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which are applicable may be in standard, concentrated or even highly concentrated form even to the extent that such products may in certain aspect be non-aqueous.

As used herein, articles such as "a" and "an" when used in a claim, are understood to mean one or more of what is claimed or described.

As used herein, the terms "include", "includes" and "including" are meant to be non-limiting.

As used herein, the term "solid" includes granular, powder, bar and tablet product forms.

As used herein, the term "fluid" includes liquid, gel, paste and gas product forms.

As used herein, the term "situs" includes paper products, fabrics, garments, hard surfaces, hair and skin.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

High Efficiency Encapsulates and Slurry/Agglomerates Comprising Same

An encapsulate that may comprise a core, a wall having an outer surface and a coating, said wall encapsulating said core, said coating coating the outer surface of said wall, said coating may comprise one or more efficiency polymers having the following formula:

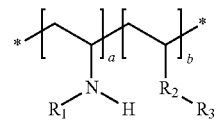

wherein:
a) wherein a and b may be integers or averages (real numbers) from about 50-100,000;
b) each R1 may be independently selected from H, $CH_3$, (C=O)H, alkylene, alkylene with unsaturated C—C bonds, $CH_2$—CROH, (C=O)—NH—R, (C=O)—$(CH_2)_n$—OH, (C=O)—R, $(CH_2)_n$-E, —($CH_2$—CH(C=O))$_n$—XR, —$(CH_2)_n$—COOH, —$(CH_2)_n$—$NH_2$, —$(CH_2)_n$—(C=O)$NH_2$, the index n may be a integer from about 0 to about 24, E may be an electrophilic group; R may be a saturated or unsaturated alkane, dialkylsiloxy, dialkyloxy, aryl, alkylated aryl, that may further contain a moiety selected from the group consisting of cyano, OH, COOH, $NH_2$, NHR, sulfonate, sulphate, —$NH_2$, quaternized amines, thiols, aldehyde, alkoxy, pyrrolidone, pyridine, imidazol, imidazolinium halide, guanidine, phosphate, monosaccharide, oligo or polysaccharide;
c) R2 or R3 can be absent or present:
  (i) when R3 is present each R2 may be independently selected from the group consisting of —$NH_2$, —COO—, —(C=O)—, —O—, —S—, —NH—(C=O)—, —$NR_1$—, dialkylsiloxy, dialkyloxy, phenylene, naphthalene, alkyleneoxy; and each R3 may be independently selected the same group as R1;
  (ii) when R3 is absent each R2 may be independently selected from the group consisting of —$NH_2$, —COO—, —(C=O)—, —O—, —S—, —NH—(C=O)—, —$NR_1$—, dialkylsiloxy, dialkyloxy, phenylene, naphthalene, alkyleneoxy; and each R3 may be independently selected the same group as R1; and
  (iii) when R2 is absent, each R3 may be independently selected the same group as R1;
d) said one or more efficiency polymers having an average molecular mass from about 1,000 Da to about 50,000,000 Da, from about 5,000 Da, to about 25,000,000 Da, from about 10,000 Da to about 10,000,000 Da, or even from about 340,000 Da to about 1,500,000 Da; a hydrolysis degree, for polyvinyl formamides, of from about 5% to about 95%, from about 7% to about 60%, or even from about 10% to about 40%; and/or a charge density from about 1 meq/g efficiency polymer to about 23 meq/g efficiency polymer, from about 1.2 meq/g efficiency polymer and 16 meq/g efficiency polymer, from about 2 meq/g efficiency polymer to about 10 meq/g efficiency polymer, or even from about 1 meq/g efficiency polymer to about 4 meq/g efficiency polymer is disclosed.

In one aspect of said encapsulate, one or more efficiency polymers is selected from the group consisting of polyvinyl amines, polyvinyl formamides, and polyallyl amines and copolymers thereof, said one or more efficiency polymers may have:
  a) an average molecular mass from about 1,000 Da to about 50,000,000 Da, from about 5,000 Da, to about 25,000,000 Da, from about 10,000 Da to about 10,000,000 Da, or even from about 340,000 Da to about 1,500,000 Da;
  b) a hydrolysis degree, for said polyvinyl formamides, of from about 5% to about 95%, from about 7% to about 60%, or even from about 10% to about 40%; and/or
  c) a charge density from about 1 meq/g efficiency polymer to about 23 meq/g efficiency polymer, from about 1.2 meq/g efficiency polymer and 16 meq/g efficiency polymer, from about 2 meq/g efficiency polymer to about 10 meq/g efficiency polymer, or even from about 1 meq/g efficiency polymer to about 4 meq/g efficiency polymer.

In one aspect of said encapsulate, said coating may comprise one or more polyvinyl formamides said polyvinyl formamides that may have:
  a) an average molecular mass from about 1,000 Da to about 50,000,000 Da, from about 5,000 Da, to about 25,000,000 Da, from about 10,000 Da to about 10,000,000 Da, or even from about 340,000 Da to about 1,500,000 Da;
  b) a hydrolysis degree, for said polyvinyl formamides, of from about 5% to about 95%, from about 7% to about 60%, or even from about 10% to about 40%; and
  c) a charge density from about 1 meq/g efficiency polymer to about 23 meq/g efficiency polymer, from about 1.2 meq/g efficiency polymer and 16 meq/g efficiency polymer, from about 2 meq/g efficiency polymer to about 10 meq/g efficiency polymer, or even from about 1 meq/g efficiency polymer to about 4 meq/g efficiency polymer. In the aforementioned aspect, efficiency polymer is synonymous with polyvinyl formamide.

In one aspect of said encapsulate, said encapsulate may have a coating to wall ratio of from about 1:200 to about 1:2, from about 1:100 to about 1:4, or even from about 1:80 to about 1:10.

In one aspect of said encapsulate;
  a) said core may comprise a material selected from the group consisting of perfumes; brighteners; dyes; insect repellants; silicones; waxes; flavors; vitamins; fabric softening agents; skin care agents in one aspect, paraffins; enzymes; anti-bacterial agents; bleaches; sensates; and mixtures thereof;
  b) said wall may comprise a material selected from the group consisting of polyethylenes; polyamides; polystyrenes; polyisoprenes; polycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect alginate and/or chitosan; gelatin; shellac; epoxy resins; vinyl polymers; water insoluble inorganics; silicone; and mixtures thereof.

In one aspect of said encapsulate, said core may comprise perfume and said wall may comprise melamine formaldehyde and/or cross linked melamine formaldehyde.

In one aspect of said encapsulate, said core may comprise perfume and said wall may comprise melamine formaldehyde and/or cross linked melamine formaldehyde, poly(acrylic acid) and poly(acrylic acid-co-butyl acrylate).

In one aspect of said encapsulate, said encapsulate may comprise a perfume that may comprise one or more perfume raw materials that provides improved perfume performance under high soil conditions and in cold water. Suitable perfume materials can be found in US published patent applications 2008/0031961A1 and 2008/0994454A1. A non-limiting list of such perfume raw materials are disclosed in Table 1 below.

TABLE 1

Useful Perfume Raw Materials

| Item | Common Name | IUPAC Name |
|---|---|---|
| 1 | Methyl 2-methyl butyrate | methyl 2-methylbutanoate |
| 2 | Isopropyl 2-methyl butyrate | propan-2-yl 2-methylbutanoate |
| 3 | Ethyl-2 Methyl Butyrate | ethyl 2-methylbutanoate |
| 4 | Ethyl-2 Methyl Pentanoate | ethyl 2-methylpentanoate |
| 5 | Ethyl heptanoate | ethyl heptanoate |
| 6 | Ethyl octanoate | Ethyl octanoate |
| 7 | isobutyl hexanoate | 2-methylpropyl hexanoate |
| 8 | Amyl butyrate | pentyl butanoate |
| 9 | Amyl heptanoate | Pentyl heptanoate |
| 10 | Isoamyl isobutyrate | 3-methylbutyl 2-methylpropanoate |
| 11 | Hexyl acetate | hexyl acetate |
| 12 | hexyl butyrate | hexyl butanoate |
| 13 | hexyl isobutyrate | hexyl 2-methylpropanoate |
| 14 | hexyl isovalerate | hexyl 3-methylbutanoate |
| 15 | hexyl propionate | hexyl propanoate |
| 16 | Ethyl 2-cyclohexyl propanoate | ethyl 2-cyclohexylpropanoate |
| 17 | Ethyl 3,5,5-trimethyl hexanoate | ethyl 3,5,5-trimethylhexanoate |
| 18 | glyceryl 5-hydroxydecanoate | 2,3-dihydroxypropyl 5-hydroxydecanoate |
| 19 | Prenyl acetate | 3-methyl 2-butenyl acetate |
| 20 | 3-methyl 2-butenyl acetate | 3-methyl 2-butenyl acetate |
| 21 | methyl 3-nonenoate | methyl non-3-enoate |
| 22 | Ethyl (E)-dec-4-enoate | Ethyl (E)-dec-4-enoate |
| 23 | Ethyl (E)-oct-2-enoate | Ethyl (E)-oct-2-enoate |
| 24 | Ethyl 2,4-decadienoate | ethyl (2E,4Z)-deca-2,4-dienoate |
| 25 | Ethyl 3-octenoate | ethyl (E)-oct-3-enoate |
| 26 | Citronellyl acetate | 3,7-dimethyloct-6-enyl acetate |
| 27 | Ethyl trans-2-decenoate | ethyl (E)-dec-2-enoate |
| 28 | 2-hexen-1-yl isovalerate | [(E)-hex-2-enyl] acetate |
| 29 | 2-hexen-1-yl propionate | [(E)-hex-2-enyl] propanoate |
| 30 | 2-hexen-1-yl valerate | [(E)-hex-2-enyl] pentanoate |
| 31 | 3-hexen-1-yl (E)-2-hexenoate | [(Z)-hex-3-enyl] (E)-hex-2-enoate |

TABLE 1-continued

Useful Perfume Raw Materials

| Item | Common Name | IUPAC Name |
|---|---|---|
| 32 | 3-Hexen-1-yl 2-methyl butyrate | [(Z)-hex-3-enyl] 2-methylbutanoate |
| 33 | 3-hexen-1-yl acetate | [(Z)-hex-3-enyl] acetate |
| 34 | 3-hexen-1-yl benzoate | [(Z)-hex-3-enyl] benzoate |
| 35 | 3-hexen-1-yl formate | [(Z)-hex-3-enyl] formate |
| 36 | 3-hexen-1-yl tiglate | [(Z)-hex-3-enyl] (Z)-2-methylbut-2-enoate |
| 37 | 2-methyl butyl 2-methyl butyrate | 2-methylbutyl 2-methylbutanoate |
| 38 | Butyl isovalerate | butyl 3-methylbutanoate |
| 39 | Geranyl acetate | [(2E)-3,7-dimethylocta-2,6-dienyl] acetate |
| 40 | Geranyl butyrate | [(2E)-3,7-dimethylocta-2,6-dienyl] butanoate |
| 41 | Geranyl isovalerate | [(3E)-3,7-dimethylocta-3,6-dienyl] 3-methylbutanoate |
| 42 | Geranyl propionate | [(2E)-3,7-dimethylocta-2,6-dienyl] propanoate |
| 43 | Allyl cyclohexane acetate | prop-2-enyl 2-cyclohexylacetate |
| 44 | Allyl Cyclohexyl Propionate | prop-2-enyl 3-cyclohexylpropanoate |
| 45 | allyl cyclohexyl valerate | prop-2-enyl 5-cyclohexylpentanoate |
| 46 | benzyl octanoate | benzyl octanoate |
| 47 | cocolactone | 6-pentyl-5,6-dihydropyran-2-one |
| 48 | coconut decanone | 8-methyl-1-oxaspiro(4.5)decan-2-one |
| 49 | gamma undecalactone | 5-heptyloxolan-2-one |
| 50 | gamma-decalactone | 5-hexyloxolan-2-one |
| 51 | gamma-dodecalactone | 5-octyloxolan-2-one |
| 52 | jasmin lactone | 6-[(E)-pent-2-enyl] oxan-2-one |
| 53 | Jasmolactone | 5-[(Z)-hex-3-enyl]oxolan-2-one |
| 54 | Nonalactone | 6-butyloxan-2-one |
| 55 | 6-acetoxydihydrotheaspirane | [2a,5a(S*)]-2,6,10,10-tetramethyl-1-oxaspiro[4.5]decan-6-yl acetate |
| 56 | Phenoxyethyl isobutyrate | 2-(phenoxy)ethyl 2-methylpropanoate |
| 57 | Pivacyclene | |
| 58 | Verdox | (2-tert-butylcyclohexyl) acetate |
| 59 | cyclobutanate | 3a,4,5,6,7,7a-hexahydro-4,7-methano-1g-inden-5(or 6)-yl butyrate |
| 60 | Dimethyl Anthranilate | methyl 2-methylaminobenzoate |
| 61 | Methyl Antranilate | methyl 2-aminobenzoate |
| 62 | Octyl Aldehyde | Octanal |
| 63 | Nonanal | Nonanal |
| 64 | Decyl aldehyde | Decanal |
| 65 | Lauric Aldehyde | Dodecanal |
| 66 | Methyl Nonyl Acetaldehyde | 2-methyl undecanal |
| 67 | Methyl Octyl Acetaldehyde | 2-methyl decanal |
| 68 | 2,4-Hexadienal | (2E,4E)-hexa-2,4-dienal |
| 69 | Intreleven Aldehyde | undec-10-enal |
| 70 | Decen-1-al | (E)-dec-2-enal |
| 71 | Nonen-1-al | (E)-2-nonen-1-al |
| 72 | Adoxal | 2,6,10-trimethylundec-9-enal |
| 73 | Geraldehyde | (4Z)-5,9-dimethyldeca-4,8-dienal |
| 74 | Iso cyclo citral | 2,4,6-trimethylcyclohex-3-ene-1-carbaldehyde |
| 75 | d-limonene mainly | 1-methyl-4-prop-1-en-2-yl-cyclohexene |
| 76 | Ligustral | 2,4-dimethylcyclohex-3-ene-1-carbaldehyde |
| 77 | Myrac aldehyde | 4-(4-methylpent-3-enyl)cyclohex-3-ene-1-carbaldehyde |
| 78 | Tridecenal | tridec-2-enal |
| 79 | Triplal | 2,4-dimethyl-3-cyclohexene-1-carboxaldehyde |
| 80 | Vertoliff | 1,2-dimethylcyclohex-3-ene-1-carbaldehyde |
| 81 | Cyclal C | 2,4-dimethylcyclohex-3-ene-1-carbaldehyde |
| 82 | Anisic aldehyde | 4-methoxybenzaldehyde |
| 83 | Helional | 3-(1,3-benzodioxol-5-yl)-2-methylpropanal |
| 84 | Heliotropin | 1,3-benzodioxole-5-carbaldehyde |
| 85 | Neocaspirene | |
| 86 | Beta Naphthol Ethyl Ether | 2-ethoxynaphtalene |
| 87 | Beta Naphthol Methyl Ether | 2-methoxynaphtalene |
| 88 | hyacinth ether | 2-cyclohexyloxyethylbenzene |
| 89 | 2-heptyl cyclopentanone (fleuramone) | 2-heptylcyclopentan-1-one |
| 90 | menthone-8-thioacetate | O-[2-[(1S)-4-methyl-2-oxocyclohexyl]propan-2-yl] ethanethioate |
| 91 | Nectaryl | 2-[2-(4-methyl-1-cyclohex-3-enyl)propyl]cyclopentan-1-one |
| 92 | Phenyl Naphthyl Ketone | naphthalen-2-yl-phenylmethanone |
| 93 | decen-1-yl cyclopentanone | 2-[(2E)-3,7-dimethylocta-2,6-dienyl] cyclopentan-1-one |
| 94 | fruity cyclopentanone (veloutone) | 2,2,5-trimethyl-5-pentylcyclopentan-1-one |
| 95 | 4-methoxy-2-methyl butane thiol (blackcurrant mercaptan) | 4-methoxy-2-methylbutane-2-thiol |
| 96 | Grapefruit Mercaptan | 2-(4-methyl-1-cyclohex-3-enyl)propane-2-thiol |
| 97 | Buccoxime | N-(1,5-dimethyl-8-bicyclo [3.2.1] octanylidene)hydroxylamine |
| 98 | Labienoxime | 2,4,4,7-Tetramethyl-6,8-nonadiene-3-one oxime |
| 99 | Undecavertol | (E)-4-methyldec-3-en-5-ol |
| 100 | Decanal diethyl acetal | 1,1-diethoxydecane |

TABLE 1-continued

Useful Perfume Raw Materials

| Item | Common Name | IUPAC Name |
|---|---|---|
| 101 | Diethyl maleate | diethyl but-2-enedioate |
| 102 | Ethyl Acetoacetate | ethyl 3-oxobutanoate |
| 103 | frutonile | 2-Methyldecanenitrile |
| 104 | Methyl dioxolan | ethyl 2-(2-methyl-1,3-dioxolan-2-yl)acetate |
| 105 | Cetalox | 3a,6,6,9a-tetramethyl-2,4,5,5a,7,8,9,9b-octahydro-1H-benzo[e][1]benzofuran |
| 106 | Cyclopentol | |
| 107 | Delta-damascone | (E)-1-(2,6,6-trimethyl-1-cyclohex-3-enyl)but-2-en-1-one |
| 108 | Eucalyptol | 1,3,3-trimethyl-2-oxabicyclo[2,2,2]octane |
| 109 | Flor acetate | |
| 110 | Ionone gamma methyl | (E)-3-methyl-4-(2,6,6-trimethyl-1-cyclohex-2-enyl)but-3-en-2-one |
| 111 | Laevo trisandol | |
| 112 | Linalool | 3,7-dimethylocta-1,6-dien-3-ol |
| 113 | Violiff | [(4Z)-1-cyclooct-4-enyl] methyl carbonate |
| 114 | Cymal | 3-(4-propan-2-ylphenyl)butanal |
| 115 | Bourgeonal | 3-(4-tert-butylphenyl)propanal |

The perfume microcapsules may be contained in a perfume microcapsule slurry.

In the context of the present invention, a perfume microcapsule slurry is defined as a watery dispersion, containing from 10% to 50% by weight of the slurry of perfume microcapsules. The perfume microcapsule slurry may comprise at least 20%, more preferably at least 40%, by weight of the perfume microcapsule slurry of encapsulated perfume ingredients The perfume microcapsule slurry of the present invention may comprise a water-soluble salt, which is present as a residual impurity of the perfume microcapsule slurry. This residual impurity could be from other ingredients in the perfume microcapsule slurry, which are purchased from various suppliers. In one aspect, the perfume microcapsule slurry is purchased from a supplier. The supplier may add additional water-soluble salt to the perfume microcapsule slurry to adjust the rheology profiles of the perfume microcapsule slurries, to improve the stability of the slurry during transport and long-term storage.

In the context of the present invention, water-soluble salts herein mean water-soluble ionic compounds, composed of dissociated positively charged cations and negatively charged anions. In the context of the present invention, "water-soluble" can be defined as a solubility in demineralised water at ambient temperature and atmospheric pressure. The perfume microcapsule slurry may comprise from 1 mmol/kg to 750 mmol/kg of water-soluble salt. In another embodiment, the perfume microcapsule slurry may comprise from 10 mmol/kg to 750 mmol/kg of water-soluble salt. In yet another embodiment, the perfume microcapsule slurry may comprise from 1 to 265 mmol/kg of water-soluble salt.

In one aspect the water-soluble salts present in the perfume microcapsule slurry are formed of polyvalent cations selected from the group comprising alkaline earthmetals, transition metals or metals, together with suitable monoatomic or polyatomic anions. In another embodiment, the water-soluble salt comprises cations, the cations being selected from the group comprising Beryllium, Magnesium, Calcium, Strontium, Barium, Scandium, Titan, Iron, Copper, Aluminium, Zinc, Germanium, Tin. In another embodiment, the water-soluble salt comprises anions, the anions being selected from the group comprising Fluorine, Chlorine, Bromine, Iodine, Acetate, Carbonate, Citrate, hydroxide, Nitrate, Phosphite, phosphate and sulfate. In one embodiment, the anions are the monoatomic anions of the halogens.

In addition to the encapsulates disclosed herein, a slurry that may comprise a efficiency polymer coated encapsulate, wherein said slurry may have zeta potential of from about −10 meV to about +50 meV, preferably from about +2 meV to about +40 meV, more preferably from about +5 meV to about +25 meV or from about −40 meV to about +35 meV, preferably from about −38 meV to about +25 meV, more preferably from about −35 meV to about +10 meV is disclosed. In one aspect, said slurry may obtain the suitable level of the efficiency polymer as a result the efficiency polymer that is part of the encapsulate and/or the encapsulate comprising the efficiency polymer may be made via combining an slurry comprising encapsulate with one or more efficiency polymers In addition to the encapsulates disclosed herein, a slurry that may comprise, based on total slurry weight, a sufficient amount of efficiency polymer coated encapsulates to provide said slurry with from about 0.05% to about 10%, from about 0.1% to about 5%, from about 0.125% to about 2% of a efficiency polymer.

In one aspect, a slurry that may comprise, based total slurry weight, from about 0.01% to about 5%, from about 0.05% to about 2% or even from about 0.1% to about 1% of a polyvinyl formamide, from about 0% to about 5% $MgCl_2$, from about 0.1 to about 3% $MgCl_2$ from about 0.2% to about 2.5% $MgCl_2$ from about 0% to about 1% Xanthan gum, from about 0.05% to about 0.5%, from about 0.1% to about 0.25% Xanthan gum and one or more of the coated or uncoated encapsules is disclosed.

In one aspect of said slurry, said polyvinyl formamide may have:
  a) an average molecular mass from about 1,000 Da to about 50,000,000 Da, from about 5,000 Da, to about 25,000,000 Da, from about 10,000 Da to about 10,000,000 Da, or even from about 340,000 Da to about 1,500,000 Da;
  b) a hydrolysis degree, for said polyvinyl formamides, of from about 5% to about 95%, from about 7% to about 60%, or even from about 10% to about 40%; and
  c) a charge density from about 1 meq/g polyvinyl formamide to about 23 meq/g polyvinyl formamide, from about 1.2 meq/g polyvinyl formamide and 16 meq/g polyvinyl formamide, from about 2 meq/g polyvinyl formamide to about 10 meq/g polyvinyl formamide, or even from about 1 meq/g polyvinyl formamide to about 4 meq/g polyvinyl formamide.

In one aspect, a process of making an improved slurry comprising combining, in any order, an encapsulate, a efficiency and optionally a stabilization system and optionally a biocide is disclosed. In one aspect, said efficiency polymer may comprise polyvinyl formamide, said srablization system may comprise $MgCl_2$ and xanthan gum.

In one aspect of said process of making an improved slurry, said encapsulate and said efficiency are permitted to be in intimate contact for at least 15 minutes, for at least 1 hour, or even for at 4 hours before said slurry is used in a product or used to produce an agglomerate.

In one aspect, any of the encapsulates and/or slurries disclosed herein may be used to produce an agglomerate.

In one aspect, a process of making the agglomerate said process comprising:
 a) combining an encapsulate and/or slurry; a plasticizer, in one aspect, a plasticizer comprising water; and, optionally, a binder and/or chelant to form a mixture;
 b) combining said mixture with said dusting agent, in one aspect, a dusting agent that comprises silica, to form a material; and
 c) removing a sufficient amount of said plasticizer from said material to yield a product comprising, based on total product weight from 1% to 50% plasticizer.

In one aspect, said plasticizer comprises water.

Suitable capsules that can be turned into the high efficiency capsules disclosed herein can be made in accordance with Applicants' teaching including but not limited to Applicants' examples, the teaching of USPA 2008/0305982 A1 and/or USPA 2009/0247449 A1. Alternatively, suitable capsules can be purchased from Appleton Papers Inc. of Appleton, Wis. USA.

In addition, the materials for making the aforementioned encapsulates can be obtained from CP Kelco Corp. of San Diego, Calif., USA; BASF AG of Ludwigshafen, Germany; Rhodia Corp. of Cranbury, N.J., USA; Hercules Corp. of Wilmington, Del., USA; Agrium Inc. of Calgary, Alberta, Canada, ISP of New Jersey U.S.A., Akzo Nobel of Chicago, Ill., USA; Stroever Shellac Bremen of Bremen, Germany; Dow Chemical Company of Midland, Mich., USA; Bayer AG of Leverkusen, Germany; Sigma-Aldrich Corp., St. Louis, Mo., USA.

Suitable efficiency polymers such as polyvinylamide-polyvinylamine copolymers can be produced by selective hydrolization of the polyvinylformamide starting polymer.

Suitable efficiency polymers can also be formed by copolymerisation of vinylformamide with arcylamide, acrylic acid, acrylonitrile, ethylene, sodium acrylate, methyl acrylate, maleic anhydride, vinyl acetate, n-vinylpyrrolidine.

Suitable efficiency polymers or oligomers can also be formed by cationic polymerisation of vinylformamide with protonic acids, such as methylsulfonic acid, and or Lewis acids, such as boron trifluoride.

Suitable efficiency polymers can be obtained from BASF AG of Ludwigshafen, Germany and include Lupamin® 9010 and Lupamin® 9030.

Process of Making Encapsulates Having Coating

In one aspect, a process of making a coated encapsulate comprising combining an encapsulate, and a one or more efficiency polymers is disclosed.

In one aspect, a process of making a coated encapsulate wherein said encapsulate, when combined with said one or more efficiency polymers, is contained in a slurry is disclosed.

In one aspect, a process of making a coated encapsulate wherein a sufficient amount of efficiency polymer is combined with said slurry to provide said slurry with, based on total slurry weight, from about 0.05% to about 10%, from about 0.1% to about 5%, or even from about 0.125% to about 2% of said efficiency polymer is disclosed.

The high efficiency polymers used in making the aforementioned coated encapsulates may be the efficiency polymers described in the High Efficiency Encapsulates and Slurry/Aggolmerates Comprising Same section of the present specification.

Consumer Product

In one aspect, a consumer product comprising any of the encapsulates, agglomerate comprising such encapsulates and/or slurries disclosed herein is disclosed.

In one aspect of said consumer product, said consumer product may be a cleaning and/or treatment composition.

In one aspect of said consumer product, said consumer product may be a laundry detergent and/or fabric softener.

In one aspect of said consumer product, said consumer product may be a fluid laundry detergent. Said fluid laundry detergent may, in one aspect, comprise, based on total fluid laundry detergent weight, from about 3% to about 80%, from about 3% to about 70%, from about 5% to about 60%, or even from about 8% to about 50% water.

In one aspect of said fluid detergent, said fluid detergent may be a liquid laundry detergent.

In one aspect of said consumer product, said consumer product may be a fluid fabric softener. Said fluid fabric softener may, in one aspect, comprise, based on total fluid fabric softener weight, from about 30% to about 90%, from about 55% to about 90%, from about 65% to about 85%, or even from about 70% to about 85% water.

In one aspect of said fluid fabric softener, said fluid fabric softener may be a liquid fabric softener.

In one aspect of said consumer product, said consumer product may be solid detergent and an adjunct ingredient.

In one aspect of said consumer product, said consumer product may be a fluid beauty care product, for example a shampoo. Said fluid beauty care product may, in one aspect, comprise, based on total fluid beauty care product weight, from about 30% to about 95%, from about 55% to about 90%, or even from about 65% to about 85% water.

In one aspect of said consumer product, said consumer product may be a conditioner.

In one aspect, said consumer product may comprise a sufficient amount of slurry and/or encapsulate to provide said consumer product with an efficiency polymer level, based on total consumer product weight, of from about 0.0001% to about 0.1%, about 0.001% to about 0.1%, or even from about 0.001% to about 0.05%.

In one aspect, said consumer product may comprise a material selected from the group consisting of an anionic surfactant, cationic surfactant, silicone and mixtures thereof, said consumer product may also have:
 a) an anionic surfactant to efficiency polymer ratio of from about 100.000:1 to about 1:1, from about 25.000:1 to about 10:1, or even from about 10.000:1 to about 100:1;
 b) a cationic surfactant to efficiency polymer ratio of from about 100.000:1 to about 1:1, from about 25.000:1 to about 10:1, or even from about 10.000:1 to about 100:1; and/or
 c) a silicone to efficiency polymer ratio of from about 100.000:1 to about 1:1 from about 25.000:1 to about 10:1, or even from about 10.000:1 to about 100:1.

In one aspect, the encapsulates disclosed herein are suitable for use in consumer products, cleaning and treatment compositions and fabric and hard surface cleaning and/or treatment compositions, detergents, and highly compacted consumer products, including highly compacted fabric and hard surface cleaning and/or treatment compositions, for example highly compacted detergents that may be solids or fluids, at levels, based on total consumer product weight, from about 0.001% to about 20%, from about 0.01% to about 10%, from about 0.05% to about 5%, from about 0.1% to about 2%.

In one aspect, a consumer product comprising an adjunct ingredient selected from the group consisting of polymers, in one aspect, a cationic polymer, surfactants, builders, chelating agents, optical brighteners, dye transfer inhibiting agents, dispersants, enzymes, enzyme stabilizers, catalytic materials, bleach activators, polymeric dispersing agents, clay soil removal/anti-redeposition agents, brighteners, dye polymer conjugates; dye clay conjugates, suds suppressors, dyes, bleach catalysts, additional perfume and/or perfume delivery systems, structure elasticizing agents, fabric softeners, carriers, hydrotropes, processing aids, rheology modifiers, structurants, thickeners, pigments, water and mixtures thereof is disclosed.

In one aspect, a consumer product comprising an adjunct ingredient comprising a rheology modifier, thickener and/or structurant having a high shear viscosity, at 20 sec-1 shear rate and at 21° C., of from 1 to 7000 cps and a viscosity at low shear (0.5 sec-1 shear rate at 21° C.) of greater than 1000 cps, or even 1000 cps to 200,000 cps. In one aspect, for cleaning and treatment compositions, such rheology modifiers impart to the aqueous liquid composition a high shear viscosity, at 20 sec-1 and at 21° C., of from 50 to 3000 cps and a viscosity at low shear (0.5 sec-1 shear rate at 21° C.) of greater than 1000 cps, or even 1000 cps to 200,000 cps. In one aspect, suitable rheology modifiers, thickeners and/or structurants may be selected from the group consisting of polyacrylates, quaternized polyacrylates, polymethacrylates, polyamides, quaternized polymethacrylates, polycarboxylates, polymeric gums like pectine, alginate, arabinogalactan (gum Arabic), carrageenan, gellan gum, xanthan gum and guar gum, other non-gum polysaccharides like gellan gum, and combinations of these polymeric materials, hydroxyl-containing fatty acids, fatty esters or fatty waxes, castor oil and its derivatives, hydrogenated castor oil derivatives such as hydrogenated castor oil and hydrogenated castor wax; and mixtures thereof.

In one aspect, a consumer product said consumer product being a fluid detergent and comprising, based on total fluid detergent weight, less then about 80% water, less than about 60% to about 2% water, from about 45% to about 7% water, from about 35% to about 9% water is disclosed.

In addition to the encapsulates disclosed herein, certain perfume delivery systems may be used in the aforementioned compositions and/or consumer products. Methods of making such perfume delivery systems and methods of making such perfume delivery systems are disclosed in USPA 2007/0275866 A1. Such perfume delivery systems include: Polymer Assisted Delivery (PAD), Molecule-Assisted Delivery (MAD), Fiber-Assisted Delivery (FAD), Amine Assisted Delivery (AAD), Cyclodextrin Delivery System (CD), Starch Encapsulated Accord (SEA), Inorganic Carrier Delivery System (ZIC), Pro-Perfume (PP). Such perfume delivery systems may be used in any combination in any type of consumer product, cleaning and/or treatment composition, fabric and hard surface cleaning and/or treatment composition, detergent, and highly compact detergent.

Perfume Microcapsule

It is advantageous to add perfume in the form of encapsulated perfume ingredients to a composition, as the encapsulation of the perfume ingredients allows a controlled and eventually targeted release of the perfume ingredients. Perfume ingredients, are the individual chemical compounds that are used to make a perfume composition. A perfume composition comprises one or more perfume ingredients, the choice of type and number of ingredients being dependent upon the final desired scent. The present invention may comprise perfume microcapsules. It is well known to those skilled in the art, that perfume microcapsules release perfume ingredients during handling of fabrics and during the in wear process, providing improved longer lasting freshness on fabrics, as compared to the addition of neat perfume alone. The release of the perfume ingredients is triggered by mechanical stress breaking the capsule wall and allowing the diffusion of the encapsulated perfume ingredient.

A perfume microcapsule comprises a capsule surrounding a core, that core comprising perfume ingredients. The capsule can be made of a number of materials, but most preferred is cross-linked melamine formaldehyde. The capsule wall material may comprise a suitable resin including the reaction product of an aldehyde and an amine, suitable aldehydes include, formaldehyde. Suitable amines can include those selected from the group comprising melamine, urea, benzoguanamine, glycoluril, and mixtures thereof. Suitable melamines can include those selected from the group comprising methylol melamine, methylated methylol melamine, imino melamine and mixtures thereof. Suitable ureas can include those selected from the group comprising dimethylol urea, methylated dimethylol urea, urea-resorcinol, and mixtures thereof. In the context of the present invention, any suitable perfume ingredient may be used. Those skilled in the art will recognize suitable compatible perfume ingredients for use in the perfume microcapsules, and will know how to select combinations of ingredients to achieve desired scents.

In one aspect, at least 75%, 85% or even 90% of said perfume microcapsules may have a particle size of from about 1 microns to about 80 microns, about 5 microns to 60 microns, from about 10 microns to about 50 microns, or even from about 15 microns to about 40 microns.

At least 75%, 85% or even 90% of said perfume microcapsules may have a particle wall thickness of from about 60 nm to about 250 nm, from about 80 nm to about 180 nm, or even from about 100 nm to about 160 nm.

The liquid fabric softening compositions of the present invention comprise from 0.05% to 0.8% by weight of the liquid fabric softening composition of encapsulated perfume ingredients, present in the form of a perfume microcapsule. This amount is necessary to ensure sufficient perfume is deposited onto the fabrics. Perfume and perfume microcapsules are washed away during the laundry process. Therefore, it is important to have enough perfume in the liquid fabric softening composition to take account of the inevitable loss, yet still have sufficient deposition onto fabrics.

In one aspect, said perfume microcapsule may be spray dried.

Perfume Microcapsule Slurry and Agglomerate Adjunct Materials

For the purposes of the present invention, the non-limiting list of adjuncts illustrated hereinafter are suitable for use in the instant compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such adjuncts are in addition to the components that are supplied via Applicants' encapsulates, agglomerates and/or slurries. The precise nature of these additional components, and levels of incorporation thereof, will depend on the physical form of the composition and the nature of the operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326, 348 B1 that are incorporated by reference.

Each adjunct ingredients is not essential to Applicants' compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts are present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds, ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Hueing Agents—Fluorescent optical brighteners emit at least some visible light. In contrast, fabric hueing agents can alter the tint of a surface as they absorb at least a portion of the visible light spectrum. Suitable fabric hueing agents include dyes, dye-clay conjugates. Suitable dyes include small molecule dyes and polymeric dyes. Suitable small molecule dyes include small molecule dyes selected from the group consisting of:
(1) Tris-Azo Direct Blue Dyes of the Formula

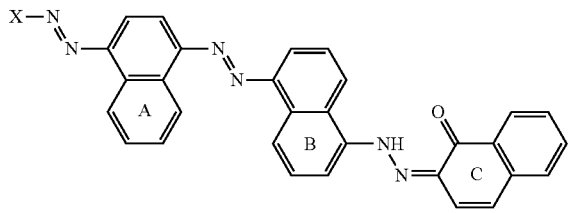

where at least two of the A, B and C napthyl rings are substituted by a sulfonate group, the C ring may be substituted at the 5 position by an $NH_2$ or NHPh group, X is a benzyl or naphthyl ring substituted with up to 2 sulfonate groups and may be substituted at the 2 position with an OH group and may also be substituted with an $NH_2$ or NHPh group.

(2) Bis-Azo Direct Violet Dyes of the Formula:

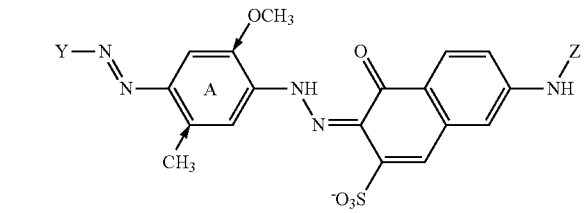

where Z is H or phenyl, the A ring is preferably substituted by a methyl and methoxy group at the positions indicated by arrows, the A ring may also be a naphthyl ring, the Y group is a benzyl or naphthyl ring, which is substituted by sulfate group and may be mono or disubstituted by methyl groups.

(3) Blue or Red Acid Dyes of the Formula

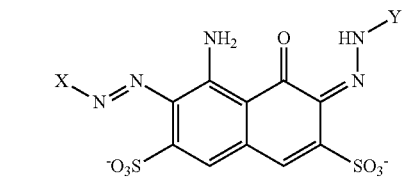

where at least one of X and Y must be an aromatic group. In one aspect, both the aromatic groups may be a substituted benzyl or naphthyl group, which may be substituted with non water-solubilising groups such as alkyl or alkyloxy or aryloxy groups, X and Y may not be substituted with water solubilising groups such as sulfonates or carboxylates. In another aspect, X is a nitro substituted benzyl group and Y is a benzyl group (4) Red Acid Dyes of the Structure

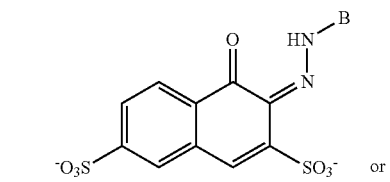

or

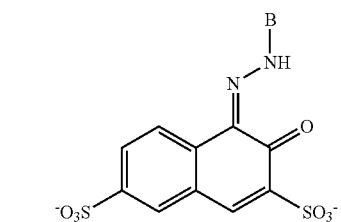

where B is a naphthyl or benzyl group that may be substituted with non water solubilising groups such as alkyl or alkyloxy or aryloxy groups, B may not be substituted with water solubilising groups such as sulfonates or carboxylates.

(5) Dis-Azo Dyes of the Structure

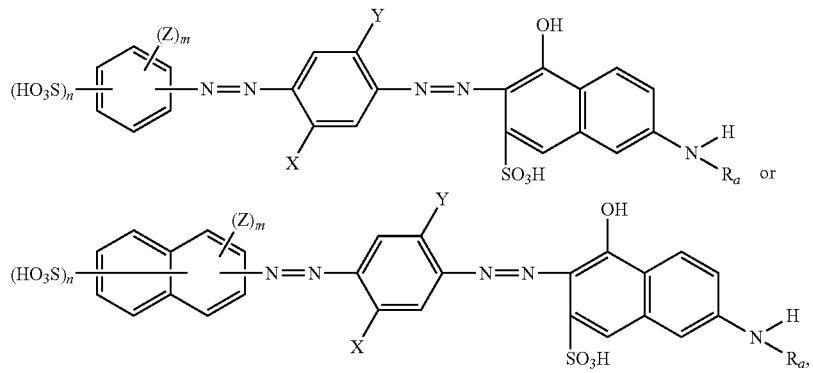

wherein X and Y, independently of one another, are each hydrogen, $C_1$-$C_4$ alkyl or $C_1$-$C_4$-alkoxy, Rα is hydrogen or aryl, Z is $C_1$-$C_4$ alkyl; $C_1$-$C_4$-alkoxy; halogen; hydroxyl or carboxyl, n is 1 or 2 and m is 0, 1 or 2, as well as corresponding salts thereof and mixtures thereof (6) Triphenylmethane Dyes of the Following Structures

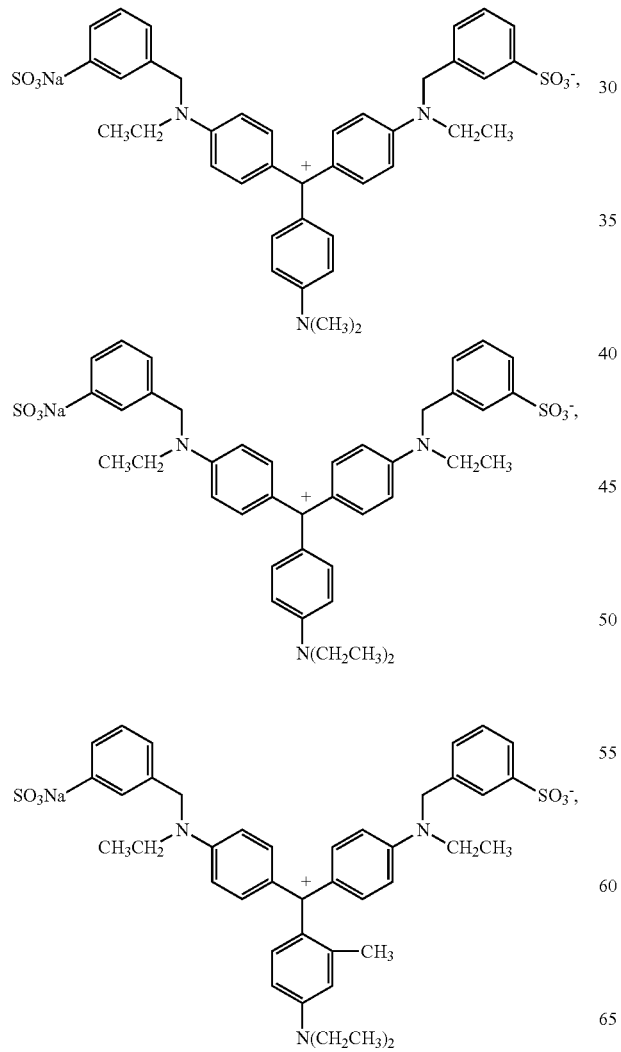

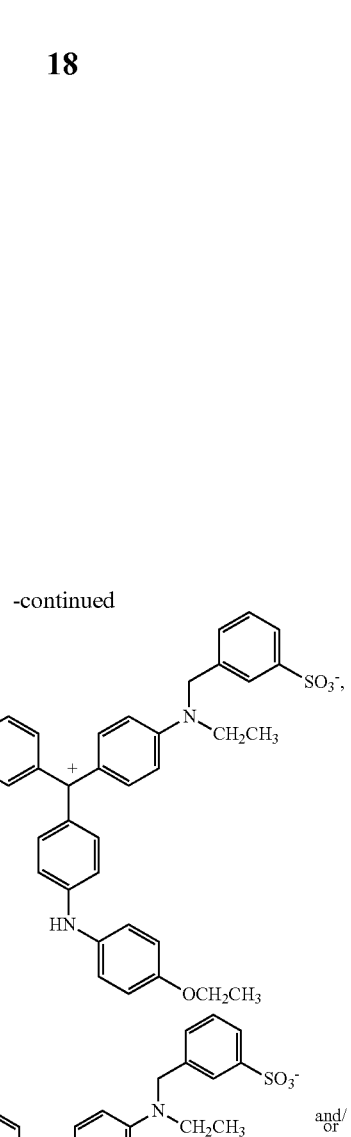

and mixtures thereof. In another aspect, suitable small molecule dyes include small molecule dyes listed below, certain of such dyes are selected from the group consisting of Colour Index (Society of Dyers and Colourists, Bradford, UK). 1,4-Naphthalenedione, 1-[2-[2-[4-[[4-(acetyloxy)butyl]ethylamino]-2-methylphenyl]diazenyl]-5-nitro-3-thienyl]-Ethanone, 1-hydroxy-2-(1-naphthalenylazo)-Naphthalenedisulfonic acid, ion(2-), 1-hydroxy-2-[[4-

(phenylazo)phenyl]azo]-Naphthalenedisulfonic acid, ion (2-), 2-[(1E)-[4-[bis(3-methoxy-3-oxopropyl)amino]-2-methylphenyl]azo]-5-nitro-3-Thiophenecarboxylic acid, ethyl ester, 2-[[4-[(2-cyanoethyl)ethylamino]phenyl]azo]-5-(phenylazo)-3-Thiophenecarbonitrile, 2-[2-[4-[(2-cyanoethyl)ethylamino]phenyl]diazenyl]-5-[2-(4-nitrophenyl)diazenyl]-3-Thiophenecarbonitrile, 2-hydroxy-1-(1-naphthalenylazo)-Naphthalenedisulfonic acid, ion(2-), 2-hydroxy-1-[[4-(phenylazo)phenyl]azo]-Naphthalenedisulfonic acid, ion(2-), 4,4'-[[4-(dimethylamino)-2,5-cyclohexadien-1-ylidene]methylene]bis[N,N-dimethyl-Benzenamine, 6-hydroxy-5-[(4-methoxyphenyl)azo]-2-Naphthalenesulfonic acid, monosodium salt, 6-hydroxy-5-[(4-methylphenyl)azo]-2-Naphthalenesulfonic acid, monosodium salt, 7-hydroxy-8-[[4-(phenylazo)phenyl]azo]-1,3-Naphthalenedisulfonic acid, ion(2-), 7-hydroxy-8-[2-(1-naphthalenyl)diazenyl]-1,3-Naphthalenedisulfonic acid, ion (2-), 8-hydroxy-7-[2-(1-naphthalenyl)diazenyl]-1,3-Naphthalenedisulfonic acid, ion(2-), 8-hydroxy-7-[2-[4-(2-phenyldiazenyl)phenyl]diazenyl]-1,3-Naphthalenedisulfonic acid, ion(2-), Acid Black 1, Acid black 24, Acid Blue 113, Acid Blue 15, Acid Blue 17, Acid Blue 25, Acid blue 29, Acid blue 3, Acid blue 40, Acid blue 45, Acid blue 62, Acid blue 7, Acid blue 75, Acid Blue 80, Acid Blue 83, Acid blue 9, Acid Blue 90, Acid green 27, Acid orange 12, Acid orange 7, Acid red 14, Acid red 150, Acid red 151, Acid red 17, Acid red 18, Acid red 266, Acid red 27, Acid red 4, Acid red 51, Acid red 52, Acid red 73, Acid red 87, Acid red 88, Acid red 92, Acid red 94, Acid red 97, Acid Violet 15, Acid Violet 17, Acid Violet 24, Acid violet 43, Acid Violet 49, Basic blue 159, Basic blue 16, Basic blue 22, Basic blue 3, Basic blue 47, Basic blue 66, Basic blue 75, Basic blue 9, Basic violet 1, Basic violet 2, Basic violet 3, Basic violet 4, Basic violet 10, Basic violet 35, C.I. Acid black 1, C.I. Acid Blue 10, C.I. Acid Blue 113, C.I. Acid Blue 25, C.I. Acid Blue 29, C.I. Acid Blue 290 C.I. Acid Red 103, C.I. Acid red 150, C.I. Acid red 52, C.I. Acid red 73, C.I. Acid red 88, C.I. Acid red 91, C.I. Acid violet 17, C.I. Acid violet 43, C.I. Direct Blue 1, C.I. Direct Blue 120, C.I. Direct Blue 34, C.I. Direct Blue 70, C.I. Direct Blue 71, C.I. Direct Blue 72, C.I. Direct Blue 82, C.I. Direct violet 51, C.I. Disperse Blue 10, C.I. Disperse Blue 100, C.I. Disperse Blue 101, C.I. Disperse Blue 102, C.I. Disperse Blue 106:1, C.I. Disperse Blue 11, C.I. Disperse Blue 12, C.I. Disperse Blue 121, C.I. Disperse Blue 122, C.I. Disperse Blue 124, C.I. Disperse Blue 125, C.I. Disperse Blue 128, C.I. Disperse Blue 130, C.I. Disperse Blue 133, C.I. Disperse Blue 137, C.I. Disperse Blue 138, C.I. Disperse Blue 139, C.I. Disperse Blue 142, C.I. Disperse Blue 146, C.I. Disperse Blue 148, C.I. Disperse Blue 149, C.I. Disperse Blue 165, C.I. Disperse Blue 165:1, C.I. Disperse Blue 165:2, C.I. Disperse Blue 165:3, C.I. Disperse Blue 171, C.I. Disperse Blue 173, C.I. Disperse Blue 174, C.I. Disperse Blue 175, C.I. Disperse Blue 177, C.I. Disperse Blue 183, C.I. Disperse Blue 187, C.I. Disperse Blue 189, C.I. Disperse Blue 193, C.I. Disperse Blue 194, C.I. Disperse Blue 200, C.I. Disperse Blue 201, C.I. Disperse Blue 202, C.I. Disperse Blue 205, C.I. Disperse Blue 206, C.I. Disperse Blue 207, C.I. Disperse Blue 209, C.I. Disperse Blue 21, C.I. Disperse Blue 210, C.I. Disperse Blue 211, C.I. Disperse Blue 212, C.I. Disperse Blue 219, C.I. Disperse Blue 220, C.I. Disperse Blue 222, C.I. Disperse Blue 224, C.I. Disperse Blue 225, C.I. Disperse Blue 248, C.I. Disperse Blue 252, C.I. Disperse Blue 253, C.I. Disperse Blue 254, C.I. Disperse Blue 255, C.I. Disperse Blue 256, C.I. Disperse Blue 257, C.I. Disperse Blue 258, C.I. Disperse Blue 259, C.I. Disperse Blue 260, C.I. Disperse Blue 264, C.I. Disperse Blue 265, C.I. Disperse Blue 266, C.I. Disperse Blue 267, C.I. Disperse Blue 268, C.I. Disperse Blue 269, C.I. Disperse Blue 270, C.I. Disperse Blue 278, C.I. Disperse Blue 279, C.I. Disperse Blue 281, C.I. Disperse Blue 283, C.I. Disperse Blue 284, C.I. Disperse Blue 285, C.I. Disperse Blue 286, C.I. Disperse Blue 287, C.I. Disperse Blue 290, C.I. Disperse Blue 291, C.I. Disperse Blue 294, C.I. Disperse Blue 295, C.I. Disperse Blue 30, C.I. Disperse Blue 301, C.I. Disperse Blue 303, C.I. Disperse Blue 304, C.I. Disperse Blue 305, C.I. Disperse Blue 313, C.I. Disperse Blue 315, C.I. Disperse Blue 316, C.I. Disperse Blue 317, C.I. Disperse Blue 321, C.I. Disperse Blue 322, C.I. Disperse Blue 324, C.I. Disperse Blue 328, C.I. Disperse Blue 33, C.I. Disperse Blue 330, C.I. Disperse Blue 333, C.I. Disperse Blue 335, C.I. Disperse Blue 336, C.I. Disperse Blue 337, C.I. Disperse Blue 338, C.I. Disperse Blue 339, C.I. Disperse Blue 340, C.I. Disperse Blue 341, C.I. Disperse Blue 342, C.I. Disperse Blue 343, C.I. Disperse Blue 344, C.I. Disperse Blue 345, C.I. Disperse Blue 346, C.I. Disperse Blue 351, C.I. Disperse Blue 352, C.I. Disperse Blue 353, C.I. Disperse Blue 355, C.I. Disperse Blue 356, C.I. Disperse Blue 357 C.I. Disperse Blue 358, C.I. Disperse Blue 36, C.I. Disperse Blue 360, C.I. Disperse Blue 366, C.I. Disperse Blue 368, C.I. Disperse Blue 369, C.I. Disperse Blue 371, C.I. Disperse Blue 373, C.I. Disperse Blue 374, C.I. Disperse Blue 375, C.I. Disperse Blue 376, C.I. Disperse Blue 378, C.I. Disperse Blue 38, C.I. Disperse Blue 42, C.I. Disperse Blue 43, C.I. Disperse Blue 44, C.I. Disperse Blue 47, C.I. Disperse Blue 79, C.I. Disperse Blue 79:1, C.I. Disperse Blue 79:2, C.I. Disperse Blue 79:3, C.I. Disperse Blue 82, C.I. Disperse Blue 85, C.I. Disperse Blue 88, C.I. Disperse Blue 90, C.I. Disperse Blue 94, C.I. Disperse Blue 96, C.I. Disperse Violet 10, C.I. Disperse Violet 100, C.I. Disperse Violet 102, C.I. Disperse Violet 103, C.I. Disperse Violet 104, C.I. Disperse Violet 106, C.I. Disperse Violet 107, C.I. Disperse Violet 12, C.I. Disperse Violet 13, C.I. Disperse Violet 16, C.I. Disperse Violet 2, C.I. Disperse Violet 24, C.I. Disperse Violet 25, C.I. Disperse Violet 3, C.I. Disperse Violet 33, C.I. Disperse Violet 39, C.I. Disperse Violet 42, C.I. Disperse Violet 43, C.I. Disperse Violet 45, C.I. Disperse Violet 48, C.I. Disperse Violet 49, C.I. Disperse Violet 5, C.I. Disperse Violet 50, C.I. Disperse Violet 53, C.I. Disperse Violet 54, C.I. Disperse Violet 55, C.I. Disperse Violet 58, C.I. Disperse Violet 6, C.I. Disperse Violet 60, C.I. Disperse Violet 63, C.I. Disperse Violet 66, C.I. Disperse Violet 69, C.I. Disperse Violet 7, C.I. Disperse Violet 75, C.I. Disperse Violet 76, C.I. Disperse Violet 77, C.I. Disperse Violet 82, C.I. Disperse Violet 86, C.I. Disperse Violet 88, C.I. Disperse Violet 9, C.I. Disperse Violet 91, C.I. Disperse Violet 92, C.I. Disperse Violet 93, C.I. Disperse Violet 93:1, C.I. Disperse Violet 94, C.I. Disperse Violet 95, C.I. Disperse Violet 96, C.I. Disperse Violet 97, C.I. Disperse Violet 98, C.I. Disperse Violet 99, C.I. Reactive Black 5, C.I. Reactive Blue 19, C.I. Reactive Blue 4, C.I. Reactive Red 2, C.I. Solvent Blue 43, C.I. Solvent Blue 43, C.I. Solvent Red 14, C.I. Acid black 24, C.I. Acid blue 113, C.I. Acid Blue 29, C.I. Direct violet 7, C.I. Food Red 14, Dianix Violet CC, Direct blue 1, Direct Blue 71, Direct blue 75, Direct blue 78, Direct blue 80, Direct blue 279, Direct violet 11, Direct violet 31, Direct violet 35, Direct violet 48, Direct violet 5, Direct Violet 51, Direct violet 66, Direct violet 9, Disperse Blue 106, Disperse blue 148, Disperse blue 165, Disperse Blue 3, Disperse Blue 354, Disperse Blue 364, Disperse blue 367, Disperse Blue 56, Disperse Blue 77, Disperse Blue 79, Disperse blue 79:1, Disperse Red 1, Disperse Red 15, Disperse Violet 26, Disperse Violet 27, Disperse Violet 28, Disperse violet 63, Disperse violet 77, Eosin Y, Ethanol, 2,2'-[[4-[(3,5-dinitro-2-thienyl)azo]phenyl]imino]bis-, diacetate (ester), Lumogen F Blue 650, Lumogen F Violet 570, N-[2-[2-(3-acetyl-5-nitro-2-thienyl)diazenyl]-5-(diethylamino)phenyl]-Acetamide, N-[2-[2-(4-chloro-3-cyano-5-formyl-2-thienyl)diazenyl]-5-(diethylamino)phenyl]-Acetamide, N-[5-[bis(2-methoxyethyl)amino]-2-[2-(5-nitro-2,1-benzisothiazol-3-yl)diazenyl]phenyl]-Acetamide, N-[5-[bis[2-(acetyloxy)ethyl]amino]-2-[(2-bromo-4,6-dinitrophenyl)azo]phenyl]-Acetamide, Naphthalimide, derivatives, Oil Black 860, Phloxine B, Pyrazole, Rose Bengal, Sodium 6-hydroxy-5-(4-isopropylphenylazo)-2-naphthalenesulfonate, Solvent Black 3, Solvent Blue 14, Solvent Blue 35, Solvent Blue 58, Solvent Blue 59, Solvent Red 24, Solvent Violet 13, Solvent Violet 8, Sudan Red 380, Triphenylmethane, and Triphenylmethane, derivatives and mixtures thereof.

Additional suitable hueing agents include, but are not limited to, thiophenes and thiazoliums described below. Suitable thiophenes may be characterized by the following structure:

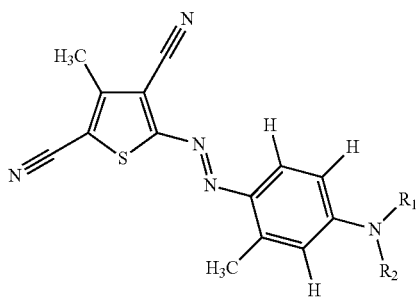

Wherein $R_1$ and $R_2$ can independently be selected from:
a) $[(CH_2CR'HO)_x(CH_2CR''HO)_yH]$
wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein $x+y \leq 5$; wherein $y \geq 1$; and wherein z=0 to 5;
b) $R_1$=alkyl, aryl or aryl alkyl and $R_2$=$[(CH_2CR'HO)_x(CH_2CR''HO)_yH]$
wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein $x+y \leq 10$; wherein $y \geq 1$; and wherein z=0 to 5;
c) $R_1$=$[CH_2CH_2(OR_3)CH_2OR_4]$ and $R_2$=$[CH_2CH_2(OR_3)CH_2OR_4]$
wherein $R_3$ is selected from the group consisting of H, $(CH_2CH_2O)_zH$, and mixtures thereof; and
wherein z=0 to 10;
wherein $R_4$ is selected from the group consisting of $(C_1-C_{16})$ alkyl, aryl groups, and mixtures thereof; and
d) wherein R1 and R2 can independently be selected from the amino addition product of styrene oxide, glycidyl methyl ether, isobutyl glycidyl ether, isopropylglycidyl ether, t-butyl glycidyl ether, 2-ethylhexylglycidyl ether, and glycidylhexadecyl ether, followed by the addition of from 1 to 10 alkylene oxide units.

In one aspect, such thiophenes may be characterized by the following structure:

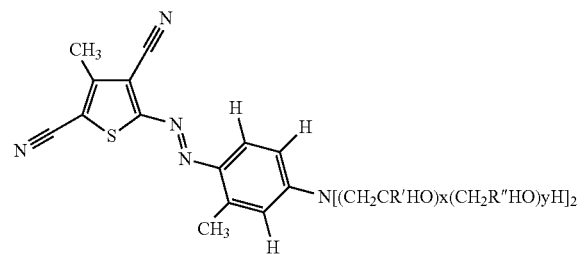

wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein $x+y \leq 5$; wherein $y \geq 1$; and wherein z=0 to 5.

Suitable thiazolium dyes include azo dyes that may have Formula (I) below:

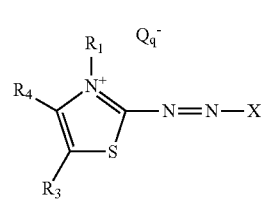

Formula I wherein:
$R_3$ and $R_4$ may be identical or different and, independently of one another, are hydrogen, a saturated or unsaturated $(C_1-C_{22})$-alkyl group, a $(C_1-C_{22})$-alkyl group substituted by a halogen atom, a hydroxy-$(C_2-C_{22})$-alkyl group optionally interrupted by oxygen, a polyether group derived from ethylene oxide, propylene oxide or butylene oxide, an amino-$(C_1-C_{22})$-alkyl group, a substituted or unsubstituted phenyl group or a benzyl group, a $(C_1-C_{22})$-alkyl group terminated in sulfonate, sulfate, or carboxylate, or the radical groups $R_3$ and $R_4$, together with the remaining molecule, can form a heterocyclic or carbocyclic, saturated or unsaturated, substituted or unsubstituted ring system optionally substituted by halogen, sulfate, sulfonate, phosphate, nitrate, and carboxylate;
X may be a radical group of the phenol series or a heterocyclic radical group or aniline series or m-toluidine series that may have Formula II below;

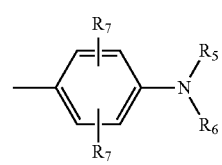

Formula II wherein:
$R_5$ and $R_6$ may be identical or different and, independently of one another, are a straight or branched saturated or unsaturated $(C_1-C_{22})$-alkyl group, a $(C_1-C_{22})$-alkyl ether group, a hydroxy-$(C_2-C_{22})$-alkyl group optionally interrupted by oxygen, a polyether group derived from ethylene oxide, propylene oxide, butylene oxide, glycidyl or combinations thereof, an amino-$(C_1-C_{22})$-alkyl group, a substituted or unsubstituted phenyl group or a benzyl group, a linear or branched $(C_1-C_{22})$-alkyl group terminated in a linear or branched $(C_1-C_{22})$-alkyl, hydroxyl, acetate, sulfonate, sulfate, or carboxylate, group or $R_5$ and $R_6$ or $R_5$ and $R_7$ or $R_6$ and $R_7$, together with the nitrogen atom, form a 5-membered to 6-membered ring system, which may comprise a further heteroatom; or $R_5$ and $R_6$ or $R_5$ and $R_7$ or $R_6$ and $R_7$, form with a carbon atom of the benzene ring an optionally oxygen-containing or nitrogen containing five or six-membered heterocycle which may be substituted with one or more $(C_1-C_{22})$-alkyl group;
$R_7$ may be identical or different and, independently of one another, are hydrogen, a halogen atom, a saturated or unsaturated $(C_1-C_{22})$-alkyl group, a $(C_1-C_{22})$-alkyl ether group, a hydroxyl group, a hydroxy-$(C_1-C_{22})$-alkyl group, a $(C_1-C_{22})$-alkoxy group, a cyano group, a nitro group, an amino group, a $(C_1-C_{22})$-alkylamino group, a $(C_1-C_{22})$-dialkylamino group, a carboxylic acid group, a $C(O)O-(C_1-C_{22})$-alkyl group, a substituted or unsubstituted C(O)O-phenyl group;

$Q^-$ may be an anion that balances the overall charge of the compound of Formula I, and the index q may be either 0 or 1. Suitable anions include chloro, bromo, methosulfate, tetrafluoroborate, and acetate anions.

$R_1$ may be a $(C_1-C_{22})$-alkyl, an alkyl aromatic or an alkyl sulfonate radical having Formula (III) below;

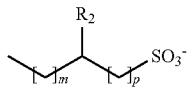

Formula III wherein
  $R_2$ is hydrogen, methyl, ethyl, propyl, acetate or a hydroxyl group;
  m and p are integers from 0 to (n−1), n is an integer from 1 to 6 and m+p=(n−1);

with the proviso that the heterocycle of the Formula (I) comprises at least two and at most three heteroatoms, where the heterocycle has at most one sulfur atom;

In one aspect, a suitable thiazolium dye may have Formula IV below:

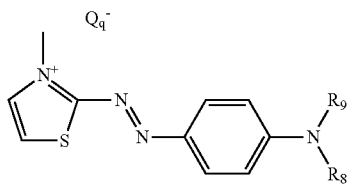

Formula IV wherein $R_8$ and $R_9$ may be identical or different and, independently of one another, may be a saturated or unsaturated $(C_1-C_{22})$-alkyl group, a $(C_1-C_{22})$-alkyl group, a hydroxy-$(C_2-C_{22})$-alkyl group optionally interrupted by oxygen, a polyether group derived from ethylene oxide, propylene oxide or butylene oxide, an amino-$(C_1-C_{22})$-alkyl group, a substituted or unsubstituted phenyl group or a benzyl group, a $(C_1-C_{22})$-alkyl group terminated in sulfonate, sulfate, or carboxylate, or $R_8$ and $R_9$, together with the nitrogen atom, may form a 5-membered to 6-membered ring system, which may comprise a further heteroatom; or $R_8$ or $R_9$ may form, with a carbon atom of the benzene ring, an optionally oxygen-containing or nitrogen containing five or six-membered heterocycle which may be substituted with one or more $(C_1-C_{22})$-alkyl groups, and mixtures thereof, and $R_{10}$ is hydrogen or methyl. For Formula IV, $Q^-$ is as described for Formula I above.

In one aspect, suitable thiazolium dyes may have Formula (V);

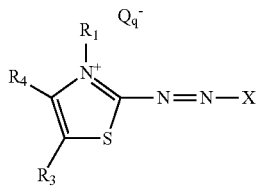

Formula V wherein:
a.) $R_1$ may be selected from a branched or unbranched $(C_1-C_{22})$-alkyl moiety, an aromatic alkyl moiety, a polyalkylene oxide moiety or a moiety having Formula (VI) below;

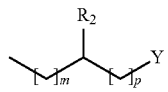

Formula VI wherein
  (i) $R_2$ may be selected from hydrogen, methyl, ethyl, propyl, acetate or a hydroxyl moiety; m and p may be, independently, integers from 0 to (n−1), with the proviso that n is an integer from 1 to 6 and m+p=(n−1)
  (ii) Y may be selected from a hydroxyl, sulfonate, sulfate, carboxylate or acetate moiety;

b.) $R_3$ and $R_4$:
  i.) may be independently selected from hydrogen; a saturated or unsaturated $(C_1-C_{22})$-alkyl moiety; a hydroxy-$(C_2-C_{22})$-alkyl moiety; a hydroxy-$(C_2-C_{22})$-alkyl moiety comprising, in addition to the hydroxyl oxygen, an oxygen atom; a polyether moiety; an amino-$(C_1-C_{22})$-alkyl moiety; a substituted or unsubstituted phenyl moiety; a substituted or unsubstituted benzyl moiety; a $(C_1-C_{22})$-alkyl moiety terminated in sulfonate, sulfate, acetate, or carboxylate; or
  ii.) when taken together may form a saturated or unsaturated heterocyclic or carbocyclic moiety; or
  iii.) when taken together may form a saturated or unsaturated heterocyclic or carbocyclic moiety substituted by, sulfate, sulfonate, phosphate, nitrate, and carboxylate;

c.) X may be moiety having Formula VII below;

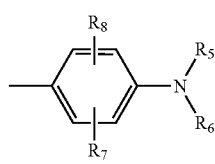

Formula VII wherein:
i.) $R_5$ and $R_6$:
  (a) may be independently selected from hydrogen; a saturated or unsaturated $(C_1-C_{22})$-alkyl moiety; a hydroxy-$(C_2-C_{22})$-alkyl moiety; a hydroxy-$(C_2-C_{22})$-alkyl moiety comprising, in addition to the hydroxyl oxygen, an oxygen atom; a capped or uncapped polyether moiety; an amino-$(C_1-C_{22})$-alkyl moiety; a substituted or unsubstituted phenyl moiety; a substituted or unsubstituted benzyl moiety; a $(C_1-C_{22})$-alkyl moiety comprising a terminating $C_1-C_4$ alkyl ether, sulfonate, sulfate, acetate or carboxylate moiety; a thiazole moiety or
  (b) when taken together may form a saturated or unsaturated heterocyclic moiety; or
  (c) when taken together form a saturated or unsaturated heterocyclic moiety substituted by one or more, alkoxylate, sulfate, sulfonate, phosphate, nitrate, and/or carboxylate moieties;
  (d) when taken together with $R_7$, $R_8$, or $R_7$ and $R_8$ form one or more saturated or unsaturated heterocyclic moieties, optionally substituted by one or more alkoxylate, sulfate, sulfonate, phosphate, nitrate, and/or carboxylate moieties; or
(e) when taken together form a thiazole moiety;
ii.) $R_7$ and $R_8$ may be independently selected from hydrogen or a saturated or unsaturated alkyl moiety;
d.) $Q^-$ may be an anion that balances the overall charge of the compound of Formula I, and the index q is 0 or 1. Suitable anions include chloro, bromo, methosulfate, tetrafluoroborate, and acetate anions.

In one aspect, for Formula V:
a.) $R_1$ may be a methyl moiety;
b.) $R_3$ and $R_4$ may be hydrogen; and
c.) X may have Formula VIII below:

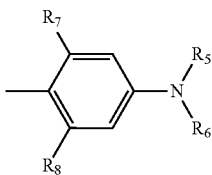

Formula VIII wherein
(i) $R_5$ and $R_6$ may be as defined for Formula VII above;
(ii) $R_7$ may be hydrogen or a methyl moiety; and
(iii) $R_8$ may be hydrogen.

In one aspect, for Formula VII $R_5$ and $R_6$ each comprise, independently, from 1 to 20 alkylene oxide units and, independently, a moiety selected from the group consisting of: styrene oxide, glycidyl methyl ether, isobutyl glycidyl ether, isopropylglycidyl ether, t-butyl glycidyl ether, 2-ethylhexylgycidyl ether, or glycidylhexadecyl ether.

Suitable polymeric dyes include polymeric dyes selected from the group consisting of polymers containing conjugated chromogens (dye-polymer conjugates) and polymers with chromogens co-polymerised into the backbone of the polymer and mixtures thereof.

In another aspect, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® (Milliken, Spartanburg, S.C. USA) Violet Conn., carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by $C_1$-$C_3$-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof. In another aspect, suitable pigments include pigments selected from the group consisting of Ultramarine Blue (C.I. Pigment Blue 29), Ultramarine Violet (C.I. Pigment Violet 15) and mixtures thereof.

The aforementioned fabric hueing agents can be used in combination (any mixture of fabric hueing agents can be used). Suitable fabric hueing agents can be purchased from Aldrich, Milwaukee, Wis., USA; Ciba Specialty Chemicals, Basel, Switzerland; BASF, Ludwigshafen, Germany; Dayglo Color Corporation, Mumbai, India; Organic Dyestuffs Corp., East Providence, R.I., USA; Dystar, Frankfurt, Germany; Lanxess, Leverkusen, Germany; Megazyme, Wicklow, Ireland; Clariant, Muttenz, Switzerland; Avecia, Manchester, UK and/or made in accordance with the examples contained herein.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include manganese, iron and chromium. Suitable MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Rheology Modifier

The liquid compositions of the present invention may comprise a rheology modifier. The rheology modifier may be selected from the group consisting of non-polymeric crystalline, hydroxy-functional materials, polymeric rheology modifiers which impart shear thinning characteristics to the aqueous liquid matrix of the composition. In one aspect, such rheology modifiers impart to the aqueous liquid composition a high shear viscosity, at 20 sec$^{-1}$ shear rate and at 21° C., of from 1 to 7000 cps and a viscosity at low shear (0.5 sec$^{-1}$ shear rate at 21° C.) of greater than 1000 cps, or even 1000 cps to 200,000 cps. In one aspect, for cleaning and treatment compositions, such rheology modifiers impart to the aqueous liquid composition a high shear viscosity, at 20 sec$^{-1}$ and at 21° C., of from 50 to 3000 cps and a viscosity at low shear (0.5 sec$^{-1}$ shear rate at 21° C.) of greater than 1000 cps, or even 1000 cps to 200,000 cps. Viscosity according to the present invention is measured using an AR 2000 rheometer from TA instruments using a plate steel spindle having a plate diameter of 40 mm and a gap size of 500 μm. The high shear viscosity at 20 sec$^{-1}$ and low shear viscosity at 0.5 sec$^{-1}$ can be obtained from a logarithmic shear rate sweep from 0.1 sec$^{-1}$ to 25 sec$^{-1}$ in 3 minutes time at 21° C. Crystalline hydroxyl functional materials are rheology modifiers which form thread-like structuring systems throughout the matrix of the composition upon in situ crystallization in the matrix. Polymeric rheology modifiers are preferably selected from polyacrylates, polymeric gums, other non-gum polysaccharides, and combinations of these polymeric materials.

Generally the rheology modifier will comprise from 0.01% to 1% by weight, preferably from 0.05% to 0.75% by weight, more preferably from 0.1% to 0.5% by weight, of the compositions herein.

Structuring agents which are especially useful in the compositions of the present invention may comprise non-polymeric (except for conventional alkoxylation), crystalline hydroxy-functional materials which can form thread-like structuring systems throughout the liquid matrix when they are crystallized within the matrix in situ. Such materials can be generally characterized as crystalline, hydroxyl-containing fatty acids, fatty esters or fatty waxes. In one aspect, rheology modifiers include crystalline, hydroxyl-containing rheology modifiers include castor oil and its derivatives. In one aspect, rheology modifiers include may be hydrogenated castor oil derivatives such as hydrogenated castor oil and hydrogenated castor wax. Commercially available, castor oil-based, crystalline, hydroxyl-containing rheology modifiers include THIXCIN™ from Rheox, Inc. (now Elementis).

Other types of rheology modifiers, besides the non-polymeric, crystalline, hydroxyl-containing rheology modifiers described heretofore, may be utilized in the liquid detergent compositions herein. Polymeric materials which provide shear-thinning characteristics to the aqueous liquid matrix may also be employed.

Suitable polymeric rheology modifiers include those of the polyacrylate, polysaccharide or polysaccharide derivative type. Polysaccharide derivatives typically used as rheology modifiers comprise polymeric gum materials. Such gums include pectine, alginate, arabinogalactan (gum Arabic), carrageenan, gellan gum, xanthan gum and guar gum.

If polymeric rheology modifiers are employed herein, a preferred material of this type is gellan gum. Gellan gum is a heteropolysaccharide prepared by fermentation of Pseudomonaselodea ATCC 31461. Gellan gum is commercially marketed by CP Kelco U.S., Inc. under the KELCO-GEL tradename.

A further alternative and suitable rheology modifier include a combination of a solvent and a polycarboxylate polymer. More specifically the solvent may be an alkylene glycol. In one aspect, the solvent may comprise dipropylene glycol. In one aspect, the polycarboxylate polymer may comprise a polyacrylate, polymethacrylate or mixtures thereof. In one aspect, solvent may be present, based on total composition weight, at a level of from 0.5% to 15%, or from 2% to 9% of the composition. In one aspect, polycarboxylate polymer may be present, based on total composition weight, at a level of from 0.1% to 10%, or from 2% to 5%. In one aspect, the solvent component may comprise mixture of dipropylene glycol and 1,2-propanediol. In one aspect, the ratio of dipropylene glycol to 1,2-propanediol may be 3:1 to 1:3, or even 1:1. In one aspect, the polyacrylate may comprise a copolymer of unsaturated mono- or di-carbonic acid and $C_1$-$C_{30}$ alkyl ester of the (meth)acrylic acid. In another aspect, the rheology modifier may comprise a polyacrylate of unsaturated mono- or di-carbonic acid and $C_1$-$C_{30}$ alkyl ester of the (meth)acrylic acid. Such copolymers are available from Noveon Inc under the tradename Carbopol Aqua 30®.

In the absence of rheology modifier and in order to impart the desired shear thinning characteristics to the liquid composition, the liquid composition can be internally structured through surfactant phase chemistry or gel phases.

Silicone Emulsion

The compositions of the present invention can comprise a silicone emulsion. An emulsion is a mixture of one liquid (the dispersed phase) dispersed in another (the continuous phase). In the context of the present, silicone emulsion also encompasses macroemulsion and microemulsion.

In one embodiment, the silicone emulsion of the present invention is added as an emulsion of Silicone oil in water or a solvent containing watery solution in a range of 35-65 (w/w %). In one embodiment, the silicone emulsion of the present invention can be any silicone emulsion.

In one embodiment the mean particle size of the Silicone emulsion is 0.01 to 2 micrometer, more preferable from 0.2 to 0.8 micrometer mean particle size.

Preferably, the emulsified silicone oil is selected from the group comprising non-ionic nitrogen free silicone oils, aminofunctional silicone oils and mixtures thereof.

In one embodiment of the present invention, the silicone emulsion is an aminofunctional silicone, preferably aminodimethicone.

In a preferred embodiment of the present invention, the silicone emulsion is a non-ionic nitrogen free silicone emulsion, preferably, selected from the group comprising polydialkyl silicone, polydimethyl silicone, alkyloxylated silicone, ethoxylated silicone, propoxylated silicone, ethoxylated propoxylated silicone, quaternary silicone or derivatives thereof and mixtures thereof. In a more preferred embodiment, the non-ionic nitrogen free silicone emulsion is selected from the group comprising polydialkyl silicone, polydimethyl silicone and mixtures thereof. In one embodiment, the silicone emulsion is polydimethyl silicone.

In this preferred embodiment, wherein the silicone emulsion is polydimethyl silicone, the polydimethyl silicone has a viscosity between 0.0001 $m^2.s^{-1}$ and 0.1 $m^2.s^{-1}$, preferably between 0.0003 $m^2.s^{-1}$ and 0.06 $m^2.s^{-1}$, more preferably between 0.00035 $m^2.s^{-1}$ and 0.012 $m^2.s^{-1}$.

Suitable solvents for use in the solvent containing watery solution can be selected from the group comprising C1-C20 linear, branched, cyclic, saturated and/or unsaturated alcohols with one or more free hydroxy groups; amines, alkanolamines, and mixtures thereof. Preferred solvents are monoalcohols, diols, monoamine derivatives, glycerols, glycols, and mixtures thereof, such as ethanol, propanol, propandiol, monoethanolamine, glycerol, sorbitol, alkylene glycols, polyalkylene glycols, and mixtures thereof. Most preferred solvents are selected from the group comprising 1,2-propandiol, 1,3-propandiol, glycerol, ethylene glycol, diethyleneglycol, and mixtures thereof.

The emulsion contains a water soluble emulsifier, selected from the group of commercially available emulsifiers encompassing cationic, anionic, nonionic or zwitter-ionic emulsifiers. In a preferred embodiment of this invention the emulsifier is a nonionic surfactant.

Alternatively premixes of silicone emulsions and solvents are utilized in order to overcome process problems in terms of proper dispersion or dissolution of all ingredients throughout the composition.

Premixes of the silicone emulsion in the context of the present invention, include high internal phase emulsion ("HIPE"). That is achieved by premixing a silicone emulsion, such as polydimethyl silicone, and an emulsifier to create a HIPE, then mixing this HIPE into the composition, thereby achieving good mixing resulting in an homogeneous mixture. Such HIPEs are comprised of at least 65%, alternatively at least 70%, alternatively at least 74%, alternatively at least 80%; alternatively not greater than 95%, by weight of an internal phase (dispersed phase), wherein the internal phase may comprise a silicone emulsion. The internal phase can also be other water insoluble fabric care benefit agents that are not already pre-emulsified. The internal phase is dispersed by using an emulsifying agent. Examples of the emulsifying agent include a surfactant or a surface tension reducing polymer. In one embodiment, the range of the emulsifying agent is from at least 0.1% to 25%, alternatively from 1% to 10%, and alternatively from 2% to 6% by weight of the HIPE. In another embodiment, the emulsifying agent is water soluble and reduces the surface tension of water, at a concentration less than 0.1% by weight of deionized water, to less than 0.0007 N (70 dynes), alternatively less than 0.0006 N (60 dynes), alternatively less than 0.0005 N (50 dynes); alternatively at or greater than 0.0002 N (20 dynes). In another embodiment, the emulsifying agent is at least partially water insoluble.

The external phase (continuous phase), in one embodiment, is water, alternatively may comprise at least some water, alternatively may comprise little or no water. In another embodiment, the external phase of water may comprise from less than 35%, alternatively less than 30%, alternatively less than 25%; alternatively at least 1%, by weight of HIPE. Non-aqueous HIPEs can be prepared as well with a solvent as the external phase with low or no water present. Typical solvents include glycerin and propylene glycol.

In another embodiment, the composition is a non-concentrated composition. In this embodiment, the silicone emulsion is not, at least initially, emulsified and can be emulsified in the fabric care composition itself.

The composition of the present invention may comprise a silicone emulsion which acts to maintain the physical stability of the liquid fabric softening composition following a freeze-thaw cycle and also upon prolonged storage at low temperatures.

The silicone emulsion of the present invention is at a level from 0.5% to 10%. In another embodiment, the silicone emulsion of the present invention is at a level from 0.3% to 10%, preferably from 0.3% to 5%, and most preferably from 0.5% to 3.0% by weight of the liquid fabric softening composition.

I. Non-Ionic Nitrogen Free Silicone Emulsions:

In the context of the present invention, preferably the silicone emulsion is selected from the group comprising non-ionic nitrogen free silicone emulsions having the formulae (I), (II), (III), and mixtures thereof:

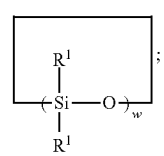
(I)

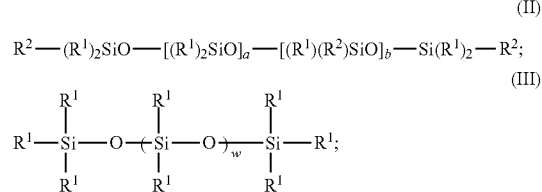

wherein each $R^1$ is independently selected from the group consisting of linear, branched or cyclic substituted or unsubstituted alkyl groups having from 1 to 20 carbon atoms; linear, branched or cyclic substituted or unsubstituted alkenyl groups having from 2 to 20 carbon atoms; substituted or unsubstituted aryl groups having from 6 to 20 carbon atoms; substituted or unsubstituted alkylaryl, substituted or unsubstituted arylalkyl and substituted or unsubstituted arylalkenyl groups having from 7 to 20 carbon atoms and mixtures thereof; each $R^2$ is independently selected from the group consisting of linear, branched or cyclic substituted or unsubstituted alkyl groups having from 1 to 20 carbon atoms; linear, branched or cyclic substituted or unsubstituted alkenyl groups having from 2 to 20 carbon atoms; substituted or unsubstituted aryl groups having from 6 to 20 carbon atoms; substituted or unsubstituted alkylaryl groups, substituted or unsubstituted arylalkyl, substituted or unsubstituted arylalkenyl groups having from 7 to 20 carbon atoms and from a poly(ethyleneoxide/propyleneoxide) copolymer group having the general formula;

$$-(CH_2)_nO(C_2H_4O)_c(C_3H_6O)_dR^3 \quad (IV)$$

polydialkyl silicone, polydimethyl silicone, alkyloxylated silicone, quaternary silicone with at least one $R^2$ being a poly(ethyleneoxy/propyleneoxy) copolymer group (ethoxylated silicone, propoxylated silicone, ethoxylated propoxylated silicone emulsions), and each $R^3$ is independently selected from the group consisting of hydrogen, an alkyl having 1 to 4 carbon atoms, an acetyl group, and mixtures thereof, wherein the index w has the value as such that the viscosity of the nitrogen-free silicone polymer of formulae (I) and (III) is between 0.0001

$m^2 \cdot s^{-1}$ (100 centistokes) and 0.1 $m^2 \cdot s^{-1}$ (100,000 centistokes); wherein a is from 1 to 50; b is from 1 to 50; n is 1 to 50; total c (for all polyalkyleneoxy side groups) has a value of from 1 to 100; total d is from 0 to 14; total c+d has a value of from 5 to 150

More preferably, the non-ionic nitrogen free silicone emulsion is selected from the group consisting of linear non-ionic nitrogen-free silicone emulsions having the formulae (II) to (III) as above, wherein $R^1$ is selected from the group consisting of methyl, phenyl, phenylalkyl, and mixtures thereof; wherein $R^2$ is selected from the group consisting of methyl, phenyl, phenylalkyl, and mixtures thereof; and from the group having the general formula (IV), as defined above, and mixtures thereof; wherein $R^3$ is defined as above and wherein the index w has a value such that the viscosity of the nitrogen-free silicone emulsion of formula (III) is between 0.0001 $m^2 \cdot s^{-1}$ (100 centistokes) and 0.1 $m^2 \cdot s^{-1}$ (100,000 centistokes); a is from 1 to 30, b is from 1 to 30, n is from 3 to 5, total c is from 6 to 100, total d is from 0 to 3, and total c+d is from 7 to 100.

Most preferably, the nitrogen-free silicone emulsion is selected from the group comprising linear non-ionic nitrogen free silicone emulsions having the general formula (III) as above, wherein $R^1$ is methyl, i.e. the silicone emulsion is polydimethyl silicone In this preferred embodiment, wherein the silicone emulsion is polydimethyl silicone, index w has a value such that the polydimethyl silicone has a viscosity between 0.0001 $m^2 \cdot s^{-1}$ and 0.1 $m^2 \cdot s^{-1}$, preferably between 0.0003 $m^2 \cdot s^{-1}$ and 0.06 $m^2 \cdot s^{-1}$, more preferably between 0.00035 $m^2 \cdot s^{-1}$ and 0.012 $m^2 \cdot s^{-1}$.

II. Aminofunctional Silicone Emulsions:

In one embodiment of the present invention, the silicone emulsion is an aminofunctional silicone. Aminofunctional silicone emulsions are materials of the formula:

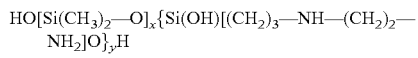

$HO[Si(CH_3)_2-O]_x\{Si(OH)[(CH_2)_3-NH-(CH_2)_2-NH_2]O\}_yH$ wherein x and y are integers which depend on the viscosity of the silicone emulsion. Preferably, the aminofunctional silicone emulsion has a molecular weight such that it exhibits a viscosity of from 0.0005 $m^2 \cdot s^{-1}$ (500 centistokes) to 0.5 $m^2 \cdot s^{-1}$ (500,000 centistokes). This material is also known as "aminodimethicone.

Method of Use

Certain of the consumer products disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with a particle according to the present invention or composition comprising said particle and then optionally washed and/or rinsed. In one aspect, a method of cleaning or treating a situs comprising optionally washing and/or rinsing said situs, contacting said situs with the composition selected from the compositions and mixtures thereof disclosed herein and optionally washing and/or rinsing said situs is disclosed. For purposes of the present invention, washing includes but is not limited to, scrubbing, and mechanical agitation. The fabric may comprise most any type of fiber capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

TEST METHODS

1.) Average Molecular Mass: For purposes of the present specification and claims, the average molecular mass of a polymer is determined in accordance with ASTM Method ASTM D4001-93(2006).
2.) Hydrolysis Degree: For purposes of the present specification and claims, hydrolysis degree is determined in accordance with the method found in U.S. Pat. No. 6,132,558, column 2, line 36 to column 5, line 25.
3.) Charge Density: For purposes of the present specification and claims, the charge density of a polymer is determined with the aid of colloid titration, cf. D. Horn, Progress in Colloid & Polymer Sci. 65 (1978), 251-264.
4.) Zeta Potential: For purposes of the present specification and claims, zeta potential is determined as follows:
 a.) Equipment: Malvern Zetasizer 3000
 b.) Procedure for sample preparation:
  (i) Add 5 drops of slurry containing the encapsulate of interest to 20 mL 1 mM NaCl solution to dilute the slurry. The concentration may need adjustment to make the count rate in the range of 50 to 300 Kcps.
  (ii) the zeta potential is measured on the diluted sample without filtration
  (iii) inject the filtered slurry in the Zetasizer cell and insert the cell in the equipment. Test temperature is set at 25° C.
  (iv) when the temperature is stable (usually in 3 to 5 minutes), measurement is started. For each sample, five measurements are taken. Three samples are taken for each slurry of interest. The average of the 15 readings is calculated.
 c.) Equipment settings for the measurements:
  Parameters settings for the sample used:
  Material: melamine RI 1,680, absorption 0.10
  Dispersant: NaCL 1 mM
  Temperature: 25° C.
  Viscosity: 0.8900 cP
  RI: 1.330
  Dielectric constant: 100
  F(ka) selection: Model: Smoluchowski F(ka) 1.5
  Use dispersant viscosity as sample viscosity
  Cell type: DTS1060C: clear disposable Zeta cells
  Measurements: 3 measurements
 d.) Results: Zeta potential is reported in mV as the average of the 15 readings taken for the slurry of interest.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

84 wt % Core/16 wt % Wall Melamine Formaldehyde (MF) Capsule 25 grams of butyl acrylate-acrylic acid copolymer emulsifier (Colloid C351, 25% solids, pka 4.5-4.7, (Kemira Chemicals, Inc. Kennesaw, Ga. U.S.A.) is dissolved and mixed in 200 grams deionized water. The pH of the solution is adjusted to pH of 4.0 with sodium hydroxide solution. 8 grams of partially methylated methylol melamine resin (Cymel 385, 80% solids, (Cytec Industries West Paterson, N.J., U.S.A.)) is added to the emulsifier solution. 200 grams of perfume oil is added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 70° C. and maintained overnight with continuous stirring to complete the encapsulation process. 23 grams of acetoacetamide (Sigma-Aldrich, Saint Louis, Mo., U.S.A.) is added to the suspension. An average capsule size of 30 um is obtained as analyzed by a Model 780 Accusizer.

Example 2

Procedure for Preparing Polymer Coated Perfume Microcapsules

Polymer coated perfume microcapsules are prepared by weighing 99 g of melamine formaldehyde perfume microcapsules reference slurry (99.75%) and the 1 g of Lupamin9030, 16% active (ex BASF, Ludwigshafen, Germany) in a glass jar. The two ingredients are shortly mixed with a spoon. They are further mixed overnight in a shaker.

Example 3

Procedure for Including Coated Perfume Microcapsules in a Liquid Laundry Detergent 74.9 g of compact liquid detergent free of perfume microcapsules is weighed and the 1.33 g of polymer coated perfume microcapsules is added.

The resulting product is mixed with a mechanical mixer for 1 minute.

Example 4

A 9 kg aliquot of perfume microcapsule slurry of Examples 2 is mixed using a Eurostar mixer (IKA) with a R1382 attachment at a constant speed of 200 RPM. To the aliquot 500 g of carboxymethyl cellulose (CP Kelco) is added while mixing using the Eurostar mixer with same attachment and speed as described above. The slurry is mixed for a total of two hours or until a uniform paste is formed.

Example 5

1.28 kg of precipitated silica Sipernat® 22S (Degussa) is added to a F-20 paddle mixer (Forberg). The mixer is run initially for 5 seconds to distribute the silica evenly on the base of the mixer. The mixer is stopped and 8.25 kg of paste, made according to Example 4, is evenly distributed onto the powder. The mixer is then run at 120 rpm for a total of 30 seconds. Following mixing, the wet particles are dumped out of the mixer and screened using a 2000 micron sieve to remove the oversize. The product passing through the screen is dried in 500 g batches in a CDT 0.02 fluid bed dryer (Niro) to a final moisture content of 20 wt % measured by Karl Fischer. The dryer is operated at an inlet temperature of 140° C. and air velocity of 0.68 m/s.

Examples 6-13

Examples of granular laundry detergent compositions comprising the perfume composition are included below.

| Raw material | % w/w of laundry detergent compositions | | | | | | | |
| --- | --- | --- | --- | --- | --- | --- | --- | --- |
| | 6 | 7 | 8 | 9 | 10 | 11 | 12 | 13 |
| Linear alkyl benzene sulphonate | 7.1 | 6.7 | 11.0 | 10.6 | 6.9 | 4.5 | 10.1 | 8.9 |
| Sodium $C_{12-15}$ alkyl ethoxy sulphate having a molar average degree of ethoxylation of 3 | 3.5 | 0.0 | 1.5 | 0.0 | 0.0 | 0.0 | 0.0 | 1.9 |
| Acrylic Acid/Maleic Acid Copolymer | 3.6 | 1.8 | 4.9 | 2.0 | 1.0 | 1.6 | 3.9 | 2.3 |
| Sodium Alumino Silicate (Zeolite 4A) | 4.0 | 0.5 | 0.8 | 1.4 | 16.3 | 0.0 | 17.9 | 2.4 |
| Sodium Tripolyphosphate | 0.0 | 17.5 | 0.0 | 15.8 | 0.0 | 23.3 | 0.0 | 0.0 |
| Sodium Carbonate | 23.2 | 16.8 | 30.2 | 17.3 | 18.4 | 9.0 | 20.8 | 30.0 |
| Sodium Sulphate | 31.4 | 29.4 | 35.5 | 7.2 | 26.3 | 42.8 | 33.2 | 28.3 |
| Sodium Silicate | 0.0 | 4.4 | 0.0 | 4.5 | 0.0 | 6.1 | 0.0 | 4.6 |
| $C_{14-15}$ alkyl ethoxylated alcohol having a molar average degree of ethoxylation of 7 | 0.4 | 2.6 | 0.8 | 2.5 | 3.1 | 0.3 | 3.8 | 0.4 |
| Sodium Percarbonate | 16.0 | 0.0 | 8.4 | 20.4 | 13.1 | 3.6 | 0.0 | 7.0 |
| Sodium Perborate | 0.0 | 9.9 | 0.0 | 0.0 | 0.0 | 0.0 | 0.0 | 0.0 |
| Tetraacetylethylenediamine (TAED) | 2.2 | 1.7 | 0.0 | 4.7 | 3.6 | 0.0 | 0.0 | 0.8 |
| Calcium Bentonite | 0.0 | 0.0 | 0.0 | 1.8 | 0.0 | 0.0 | 0.0 | 5.6 |
| Citric acid | 2.0 | 1.5 | 2.0 | 2.0 | 2.5 | 1.0 | 2.5 | 1.0 |
| Protease (84 mg active/g) | 0.14 | 0.12 | 0.0 | 0.12 | 0.09 | 0.08 | 0.10 | 0.08 |
| Amylase (22 mg active/g) | 0.10 | 0.11 | 0.0 | 0.10 | 0.10 | 0.0 | 0.14 | 0.08 |
| Lipase (11 mg active/g) | 0.70 | 0.50 | 0.0 | 0.70 | 0.50 | 0.0 | 0.0 | 0.0 |
| Cellulase (2.3 mg active/g) | 0.0 | 0.0 | 0.0 | 0.0 | 0.0 | 0.0 | 0.18 | 0.0 |
| Benefit agent composition of Example 5 | 1.4 | 0.6 | 0.8 | 1.0 | 0.7 | 0.3 | 0.7 | 1.2 |
| Water & Miscellaneous | Balance to 100% | | | | | | | |

The equipment and materials described in Examples 1 through to 19 can be obtained from the following: IKA Werke GmbH & Co. KG, Staufen, Germany; CP Kelco, Atlanta, United States; Forberg International AS, Larvik, Norway; Degussa GmbH, Düsseldorf, Germany; Niro A/S, Soeberg, Denmark; Baker Perkins Ltd, Peterborough, United Kingdom; Nippon Shokubai, Tokyo, Japan; BASF, Ludwigshafen, Germany; Braun, Kronberg, Germany; Industrial Chemicals Limited, Thurrock, United Kingdom; Primex ehf, Siglufjordur, Iceland; ISP World Headquarters; Polysciences, Inc. of Warrington, Pa., United States; Cytec Industries Inc., N.J., United States; International Specialty Products, Wayne, N.J., United States; P&G Chemicals Americas, Cincinnati, Ohio, United States; Sigma-Aldrich Corp., St. Louis, Mo., United States, Dow Chemical Company of Midland, Mich., USA Examples 14-23

Fabric Conditioner

Non-limiting examples of fabric conditioners containing the polymer coated perfume microcapsules disclosed in the present specification are summarized in the following table.

| (% wt) | \multicolumn{10}{c}{EXAMPLES} | | | | | | | | | |
|---|---|---|---|---|---|---|---|---|---|---|
| | 14 | 15 | 16 | 17 | 18 | 19 | 20 | 21 | 22 | 23 |
| FSA[a] | 14 | 16.47 | 14 | 12 | 12 | 16.47 | — | — | 5 | 10 |
| FSA[b] | | | | | — | | 3.00 | — | — | — |
| FSA[c] | | | | | — | | — | 6.5 | — | — |
| Ethanol | 2.18 | 2.57 | 2.18 | 1.95 | 1.95 | 2.57 | — | — | 0.81 | |
| Isopropyl Alcohol | — | — | — | — | — | — | 0.33 | 1.22 | — | 1.0— |
| Starch[d] | 1.25 | 1.47 | 2.00 | 1.25 | — | 2.30 | 0.5 | 0.70 | 0.71 | 0.42 |
| Phase Stabilizing Polymer[f] | 0.21 | 0.25 | 0.21 | 0.21 | 0.14 | 0.18 | 0.15 | 0.14 | 0.2 | 0.1 |
| Suds Suppressor[g] | — | — | — | — | — | — | — | 0.1 | — | — |
| Calcium Chloride | 0.15 | 0.176 | 0.15 | 0.15 | 0.30 | 0.176 | — | 0.1-0.15 | — | 0025. |
| DTPA[h] | 0.017 | 0.017 | 0.017 | 0.017 | 0.007 | 0.007 | 0.20 | — | 0.002 | 0.002 |
| Preservative (ppm)[i,j] | 5 | 5 | 5 | 5 | 5 | 5 | — | 250[j] | 5 | 5 |
| Antifoam[k] | 0.015 | 0.018 | 0.015 | 0.015 | 0.015 | 0.015 | — | — | 0.015 | 0.015 |
| Silicone[l] | 1 | — | — | 3 | — | — | — | — | 1 | — |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Polymer coated perfume microcapsules as disclosed in Example 2 | 0.2 | 0.02 | 0.1 | 0.15 | 0.12 | 0.13 | 0.3 | 0.4 | 0.24 | 0.1 |
| Additional Neat Perfume | 0.8 | 0.7 | 0.9 | 0.5 | 1.2 | 0.5 | 1.1 | 0.6 | 1.0 | 0.9 |
| Deionized Water | † | † | † | † | † | † | † | † | † | † |

[a] N,N-di(tallowoyloxyethyl)-N,N-dimethylammonium chloride.
[b] Methyl bis(tallow amidoethyl)2-hydroxyethyl ammonium methyl sulfate.
[c] Reaction product of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.
[d] Cationic high amylose maize starch available from National Starch under the trade name CATO ®.
[f] Rheovis CDE ex BASF.
[g] SE39 from Wacker
[h] Diethylenetriaminepentaacetic acid.
[i] KATHON ® CG available from Rohm and Haas Co. "PPM" is "parts per million."
[j] Gluteraldehyde
[k] Silicone antifoam agent available from Dow Corning Corp. under the trade name DC2310.
[l] Silicone emulsion, available under the trade name E3500 supplied by Wacker
† balance

Examples 24-29

Liquid Laundry Formulations (HDLs)

| Ingredient | 24 | 25 | 26 | 27 | 28 | 29 |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Glutaraldehyde | 0 | 0 | 19 ppm | 0 | 13 ppm | 0 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Silicone (PDMS) emulsion | 0.003 | 0.003 | 0.003 | 0.003 | 0.003 | 0.003 |
| Neat Perfume | 0.02 | 0.15 | 0.0 | 0.2 | 0.3 | 0.1 |
| Polymer coated perfume microcapsules as disclosed in Example 2 | 0.2 | 0.02 | 0.1 | 0.15 | 0.12 | 0.13 |
| Water | Balance | Balance | Balance | Balance | Balance | Balance |

Example 30

Shampoo Formulation

| Ingredient | |
|---|---|
| Ammonium Laureth Sulfate (AE$_3$S) | 6.00 |
| Ammonium Lauryl Sulfate (ALS) | 10.00 |
| Laureth-4 Alcohol | 0.90 |
| Trihydroxystearin [7] | 0.10 |
| Polymer coated perfume microcapsules as disclosed in Example 2 | 0.60 |
| Sodium Chloride | 0.40 |
| Citric Acid | 0.04 |
| Sodium Citrate | 0.40 |
| Sodium Benzoate | 0.25 |
| Ethylene Diamine Tetra Acetic Acid | 0.10 |
| Dimethicone [9, 10, 11] | 1.00 [9] |
| Water and Minors (QS to 100%) | Balance |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An encapsulate comprising a core which comprises perfume, a wall having an outer surface and a coating, said wall comprising melamine formaldehyde and encapsulating said core, said coating surrounding the outer surface of said wall, said coating comprising an efficiency polymer which is a polyvinyl formamide, said efficiency polymer having an average molecular mass from about 10,000 Da to about 50,000,000 Da; a hydrolysis degree, of from about 5% to about 40%; and/or a charge density from about 1 meq/g efficiency polymer to about 23 meq/g efficiency polymer.

2. An encapsulate according to claim 1, having a coating to wall ratio of from about 1:200 to about 1:2.

3. An encapsulate according to claim 1, wherein;
   a) said core further comprises a material selected from the group consisting of brighteners; dyes; insect repellants; silicones; waxes; flavors; vitamins; fabric softening agents; skin care agents enzymes; anti-bacterial agents; bleaches; sensates; and mixtures thereof;
   b) said wall further comprises a material selected from the group consisting of polyethylenes; polyamides; polystyrenes; polyisoprenes; polycarbonates; polyesters; polyacrylates; aminoplasts in addition to melamine formaldehyde, gelatin; shellac; epoxy resins; vinyl polymers; water insoluble inorganics; silicone; and mixtures thereof.

4. An encapsulate according to claim 1, wherein said wall comprises melamine formaldehyde and cross linked melamine formaldehyde.

5. An encapsulate according to claim 1, wherein said wall comprises melamine formaldehyde, cross linked melamine formaldehyde, poly(acrylic acid) and poly(acrylic acid-co-butyl acrylate).

6. An encapsulate according to claim 1, wherein said efficiency polymer has an average molecular mass from about 10,000 Da to about 10,000,000 Da.

7. A slurry comprising an encapsulate according to claim 1, said slurry having a zeta potential of from about −10 meV to about +50 meV.

8. A slurry comprising, based on total slurry weight, a sufficient amount of the encapsulate of claim 1 to provide said slurry with from about 0.05% to about 10% of the efficiency polymer.

9. An agglomerate comprising an encapsulate according to claim 1.

10. A process of making the agglomerate of claim 9, said process comprising:
    a) combining an encapsulate according to claim 1; a plasticizer, and, optionally, a binder and/or chelant to form a mixture;
    b) combining said mixture with a dusting agent; and
    c) removing a sufficient amount of said plasticizer from said material to yield a product comprising, based on total product weight from 1% to 50% plasticizer.

11. A consumer product comprising:
    a) an capsulate according to claim 1; and
    b) an adjunct ingredient.

12. The consumer product of claim 11, said consumer product comprising a sufficient amount of encapsulate to provide said consumer product with said efficiency polymer level, based on total consumer product weight, of from about 0.0001% to about 0.1%.

13. A consumer product according to claim 11, said consumer product comprising a material selected from the group consisting of an anionic surfactant, cationic surfactant, silicone and mixtures thereof.

14. A consumer product according to claim 11 wherein said adjunct ingredient is selected from the group consisting of a cationic polymer, surfactants, builders, chelating agents, optical brighteners, dye transfer inhibiting agents, dispersants, enzymes, enzyme stabilizers, catalytic materials, bleach activators, polymeric dispersing agents, clay soil removal/anti-redeposition agents, brighteners, dye polymer conjugates; dye clay conjugates, suds suppressors, dyes, bleach catalysts, additional perfume and/or perfume delivery systems, structure elasticizing agents, fabric softeners, carriers, hydrotropes, processing aids, rheology modifiers, structurants, thickeners, pigments, water and mixtures thereof.

15. A consumer product according to claim 14, said consumer product comprising a rheology modifier, thickener and/or structurant having a high shear viscosity, at 20 sec$^{-1}$ shear rate and at 21° C., of from 1 to 7000 cps and a viscosity at low shear, sec$^{-1}$ shear rate at 21° C., of greater than 1000 cps.

16. A consumer product according to claim 11, said consumer product being a fluid detergent and comprising, based on total fluid detergent weight, less than about 80% water.

17. A method of cleaning or treating a situs comprising optionally washing and/or rinsing said situs, contacting said situs with a consumer product according to claim 11, and optionally washing and/or rinsing said situs.

* * * * *